US012618062B2

(12) United States Patent
Derda et al.

(10) Patent No.: US 12,618,062 B2
(45) Date of Patent: May 5, 2026

(54) DISPLAY OF MOLECULES ON SILENTLY GENETICALLY ENCODED NANOSCALE CARRIERS FOR DETERMINING SYNERGISTIC MOLECULAR INTERACTIONS

(71) Applicant: The Governors of the University of Alberta, Edmonton (CA)

(72) Inventors: Ratmir Derda, Edmonton (CA); Nicholas Bennett, Edmonton (CA); Susmita Sarkar, Edmonton (CA)

(73) Assignee: 48Hour Discovery Inc., Edmonton (CA)

( * ) Notice: Subject to any disclaimer, the term of this patent is extended or adjusted under 35 U.S.C. 154(b) by 1290 days.

(21) Appl. No.: 16/481,319

(22) PCT Filed: Jan. 31, 2018

(86) PCT No.: PCT/CA2018/050113
§ 371 (c)(1),
(2) Date: Jul. 26, 2019

(87) PCT Pub. No.: WO2018/141058
PCT Pub. Date: Aug. 9, 2018

(65) Prior Publication Data
US 2019/0352636 A1    Nov. 21, 2019

Related U.S. Application Data

(60) Provisional application No. 62/452,744, filed on Jan. 31, 2017.

(51) Int. Cl.
| | |
|---|---|
| *C12N 15/10* | (2006.01) |
| *G01N 33/554* | (2006.01) |
| *C12Q 1/6806* | (2018.01) |
| *C40B 20/04* | (2006.01) |
| *C40B 30/04* | (2006.01) |
| *C40B 70/00* | (2006.01) |

(52) U.S. Cl.
CPC ....... *C12N 15/1037* (2013.01); *G01N 33/554* (2013.01); *C12Q 1/6806* (2013.01); *C12Y 203/01028* (2013.01); *C12Y 302/01001* (2013.01); *C40B 20/04* (2013.01); *C40B 30/04* (2013.01); *C40B 70/00* (2013.01)

(58) Field of Classification Search
CPC .. C12N 15/1037; G01N 33/554; C40B 20/04; C40B 30/04
See application file for complete search history.

(56) References Cited

U.S. PATENT DOCUMENTS

| | | | |
|---|---|---|---|
| 6,472,146 B1 | 10/2002 | Larocca et al. | |
| 7,141,366 B1 | 11/2006 | Sandman et al. | |
| 7,754,680 B2 * | 7/2010 | Cunningham | C07K 7/06 |
| | | | 530/300 |
| 9,399,653 B2 | 7/2016 | Cairo et al. | |
| 9,958,437 B2 * | 5/2018 | Derda | C12N 15/1037 |
| 2009/0137424 A1 | 5/2009 | Tsao et al. | |
| 2010/0317547 A1 | 12/2010 | Winter et al. | |
| 2015/0316561 A1 | 11/2015 | Zhang et al. | |
| 2017/0355982 A1 | 12/2017 | Derda et al. | |

FOREIGN PATENT DOCUMENTS

| | | |
|---|---|---|
| CA | 2935587 A1 | 8/2015 |
| EP | 2917174 B1 | 9/2018 |
| JP | H09-500016 A | 1/1997 |
| JP | 2001-513995 A | 9/2001 |
| JP | 2009-512443 A | 3/2009 |
| JP | 2005-536234 A | 3/2011 |
| JP | 2015-508638 A | 3/2015 |
| JP | 2015-529826 A | 10/2015 |
| JP | 2017522188 A | 8/2017 |
| JP | 2017-535260 A | 11/2017 |
| JP | 2017-536846 A | 12/2017 |
| JP | 2009-511053 A | 10/2019 |
| WO | 99/10485 | 3/1999 |
| WO | 01/23619 | 4/2001 |
| WO | 2010105363 A1 | 9/2010 |
| WO | 2010107405 A1 | 9/2010 |
| WO | 2012074130 A1 | 6/2012 |
| WO | 2013050083 A1 | 4/2013 |
| WO | 2013113127 A1 | 8/2013 |
| WO | 2014/035693 A2 | 3/2014 |
| WO | 2016/061695 | 4/2016 |
| WO | WO-2016061695 A1 * | 4/2016 ........... C12N 15/102 |

(Continued)

OTHER PUBLICATIONS

Chelius, D, et al, "Capture of Pepties with N-terminal Serine and threonine: a Sequence-specific Chemical Method for Peptide Mixture Simplification", Bioconjug Chem, 2003, vol. 14, No. 1, pp. 205-211.

Ng, Simon et al, "Bacteriophages and Viruses as a Support for Organic Synthesis and Combination Chemistry," ACS Chemical Biology, 2001, vol. 7, No. 1, pp. 123-138.

Ng, Simon, et al, "Quantitative Synthesis of Genetically Encoded Glycopeptide Libraries Displayed on M13 Phage" ACS Chemical Biology, Jun. 24, 2012, vol. 7, pp. 1482-1487, ISSN 1521-3773.

Ng et al, "Genetically encoded fragment-based discovery of glycopeptide ligands for carbohydrate-binding proteins" Journal of the American Chemical Society, Apr. 10, 2015, vol. 137, pp. 5248-5251, ISSN0002-7863.

(Continued)

*Primary Examiner* — Sahana S Kaup
(74) *Attorney, Agent, or Firm* — Bennett Jones LLP

(57) ABSTRACT

The present application provides a method of producing a "liquid" array of ligand (such as glycan) modified bacteriophage where the ligand modification is encoded genetically within the bacteriophage genome. This method will allow for the determination of the ligand binding profile of biomacromolecules and cells. Furthermore the method allows the elucidation of ligand-protein interactions where ligand binding is co-operative and synergistic.

20 Claims, 11 Drawing Sheets
Specification includes a Sequence Listing.

(56) References Cited

FOREIGN PATENT DOCUMENTS

| | | |
|---|---|---|
| WO | 2016/083793 | 6/2016 |
| WO | 2018/141058 A1 | 8/2018 |

OTHER PUBLICATIONS

Matochko, Wadim, et al, "Deep Sequencing analysis of phage libraries using Illumina platform" (2012) Methods 58 47-55.

Tjhung et al., "Silent Encoding of Chemical Post-Translational Modifications in Phage-Displayed Libraries" Journal of The American Chemical Society, vol. 138, No. 1, Dec. 28, 2015, pp. 32-35.

Schlippe, Y. V. G.; Hartman, M. C. T.; Josephson, K .; Szostak, J. W. JACS 2012, 134, 10469.

Scott, J.K. & Smith, G.P. Searching for Peptide Ligands with an Epitope Library. Science 249, 386-390 (1990).

Brenner, S.; Lerner, R. A. PNAS 1992, 89, 5381.

Santoso, B.; Lam, S.; Murray, B. W.; Chen, G. Bioorganic & Medicinal Chemistry Letters 2013, 23, 5680.

Kawakami, T.; Ishizawa, T.; Fujino, T.; Reid, P. C.; Suga, H.; Murakami, H. Acs Chemical Biology 2013, 8, 1205.

Josephson, K.; Hartman, M. C. T.; Szostak, J. W. JACS 2005, 127, 11727.

Jafari, M. R.; Deng, L.; Kitov, P. I.; Ng, S.; Matochko, W. L.; Tjhung, K. F.; Zeberoff, A.; Elias, A.; Klassen, J. S.; Derda, R. ACS Chem Biol 2014, 9, 443.

Heinis, C.; Rutherford, T.; Freund, S.; Winter, G. Nature Chemical Biology 2009, 5, 502.

Guillon, R.; Pagniez, F.; Giraud, F.; Crepin, D.; Picot, C.; Le Borgne, M.; Morio, F.; Duflos, M.; Loge, C.; Le Pape, P. ChemMedChem 2011, 6, 816-825.

Kitov, P. I.; Vinals, D. F.; Ng, S.; Tjhung, K. F.; Derda, R. J. Am. Chem. Soc. 2014, 136, 8149-8152.

Kim, Y. W.; Grossmann, T. N.; Verdine, G. L. Nature protocols 2011, 6, 761-771.

Matochko, W. L.; Cory Li, S.; Tang, S. K.; Derda, R. Nucleic Acids Res. 2014, 42, 1784-1798.

Wang, W.; Kitova, E. N.; Klassen, J. S. Anal. Chem. 2003, 75, 4945-4955.

Kitova, E. N.; El-Hawiet, A.; Schnier, P. D.; Klassen, J. S. J. Am. Soc. Mass. Spectrom. 2012, 23, 431-441.

El-Hawiet, A.; Kitova, E. N.; Klassen, J. S. Biochemistry 2012, 51, 4244-4253.

Sun, J.; Kitova, E. N.; Wang, W.; Klassen, J. S. Anal. Chem. 2006, 78, 3010-3018.

Chilkoti, A.; Tan, P. H.; Stayton, P. S. Proc. Natl. Acad. Sci. U.S.A. 1995, 92, 1754-1758.

Green, N. M. Methods Enzymol. 1990, 184, 51-67.

Askowski, R.A., Gerick, F. & Thornton, J.M. The structural basis of allosteric regulation in proteins. FEBS letters 583, 1692-1698 (2009).

Marvin, D.A., Welsh, L.C., Symmons, M.F., Scott, W.R. & Straus, S.K. Molecular structure of fd (f1, M13) filamentous bacteriophage refined with respect to X-ray fibre diffraction and solid-state NMR data supports specific models of phage assembly at the bacterial membrane. Journal of molecular biology 355, 294-309 (2006).

Ellington, A.D. & Szostak, J.W. In vitro selection of RNA molecules that bind specific ligands. Nature 346, 818-822 (1990).

Tuerk, C. & Gold, L. Systematic evolution of ligands by exponential enrichment: RNA ligands to bacteriophage T4 DNA polymerase. Science 249, 505-510 (1990).

Rakonjac, J., Bennett, N.J., Spagnuolo, J., Gagic, D. & Russel, M. Filamentous Bacteriophage: Biology, Phage Display and Nanotechnology Applications. Curr Issues Mol Biol 13, 51-75 (2011).

Shivatare, S.S. et al. Modular synthesis of N-glycans and arrays for the hetero-ligand binding analysis of HIV antibodies. Nature chemistry 8, 338-346 (2016).

Johnson, Q.R., Lindsay, R.J., Petridis, L. & Shen, T. Investigation of Carbohydrate Recognition via Computer Simulation. Molecules 20, 7700-7718 (2015).

Watanabe, M., Nakamura, O., Muramoto, K. & Ogawa, T. Allosteric regulation of the carbohydrate-binding ability of a hovel conger eel galectin by D-mannoside. The Journal of biological chemistry 287, 31061-31072 (2012).

Thomas et al. Application of Biocatalysis to on-DNA Carbohydrate Library Synthesis. ChemBioChem 2017, 18, 858.

Crimmins, D.L., S.M. Mische, and N.D. Denslow, Chemical cleavage of proteins in solution. Curr Protoc Protein Sci, 2005. 11(11).

Gardner, M.W. and U.S. Brodbelt, Impact of proline and aspartic acid residues on the dissociation of intermolecularly crosslinked peptides. J Am Soc Mass Spectrom, 2008. 19(3): p. 344-57.

Guo, Y., et al., Structural basis for distinct ligand-binding and targeting properties of the receptors DC-SIGN and DC-SIGNR. Nat Struct Mol Biol, 2004. 11(7): 591-8.

Lerner and Brenner, Encoded Combinatorial Chemistry. Proc. Natl. Acad. Sci. 1992. 89, pp. 5381-5383.

Lam et al. The "One-Bead-One-Compound" Combinatorial Library Method. Chem. Rev., 1997, 97 (2), pp. 411-448.

Boving and Hogersson. PEGylation of microbead surfaces reduces unspecific antibody binding in glycan-based suspension array. J Immunol Methods. Oct. 2014;412:42-52.

Pochechueva et al. Comparison of printed glycan array, suspension array and ELISA in the detection of human anti-glycan antibodies. Glycoconj J. Dec. 2011;28(8-9):50.

Purohit et al. Multiplex glycan bead array for high throughput and high content analyses of glycan binding proteins. Nature communications, vol. 9, Article No. 258 (2018).

Thomas F. Woiwode et al., Synthetic Compound Libraries Displayed on the Surface of Encoded Bacteriophage, Chemistry and Biology, Current Biology, Sep. 2003, pp. 847-858, vol. 10(9).

* cited by examiner

Start    Silent Distal Barcode    KpnI    N1 domain

GGAGATTTCAACGTGAAAAATTATTATTCGCAATTCCTTTATGGTACCTTTCTATTCTCACTCGGCGAAACTGTT

Y K K L F A I P L V V P F Y S H S A E T V

Degenerate Barcode CTN CTN TTY GCN ATH CCN CTN

Sequence 4 4 4 2 4 3 4 = 6144 possible sequences

| Codon | Amino Acid | Codon | Amino Acid | Codon | Amino Acid | Codon | Amino Acid |
|-------|-----------|-------|-----------|-------|-----------|-------|-----------|
| TTA | Leu | TTC | Phe | ATT | Ile | CCT | Pro |
| TTG | Leu | TTT | Phe | ATC | Ile | CCC | Pro |
| CTT | Leu | GCT | Ala | ATA | Ile | CCA | Pro |
| CTC | Leu | GCC | Ala | | | CCG | Pro |
| CTA | Leu | GCA | Ala | | | | |
| CTG | Leu | GCG | Ala | | | | |

FIGURE 1

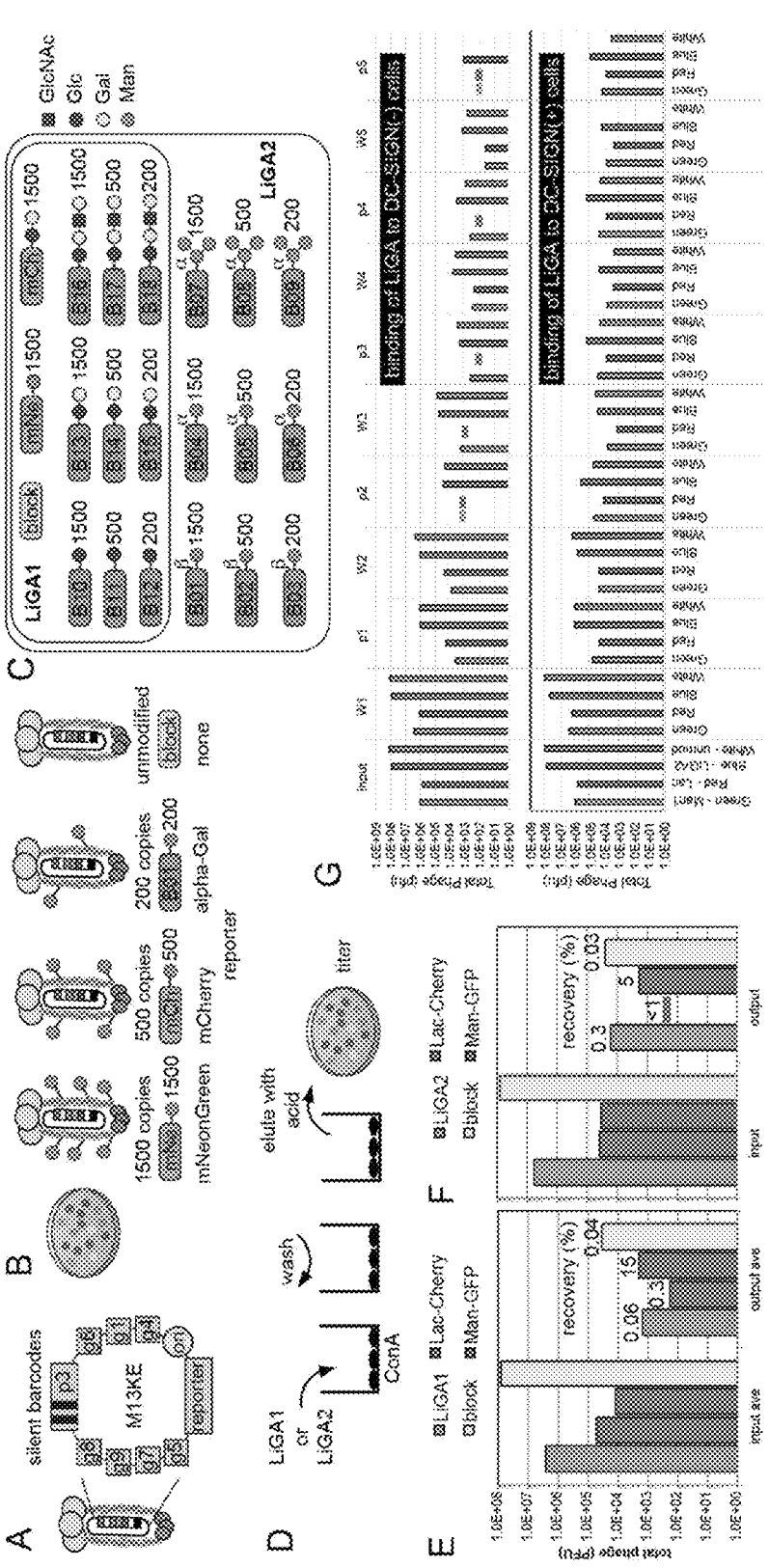
Figure 6A-G

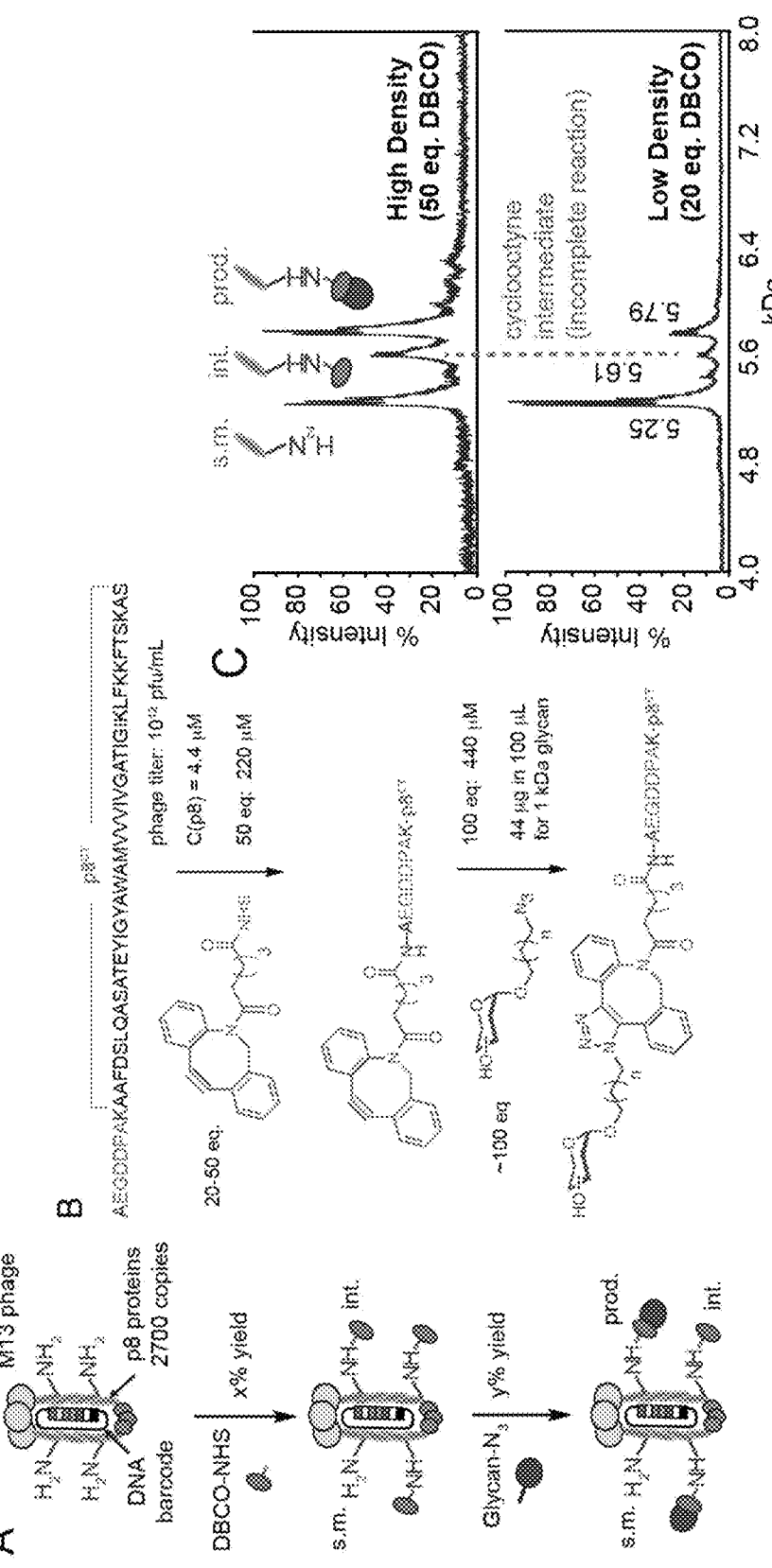
Figure 7A-C

D   ~100-150 examples of mono, di- tri-, tera-saccharides and higher glycans
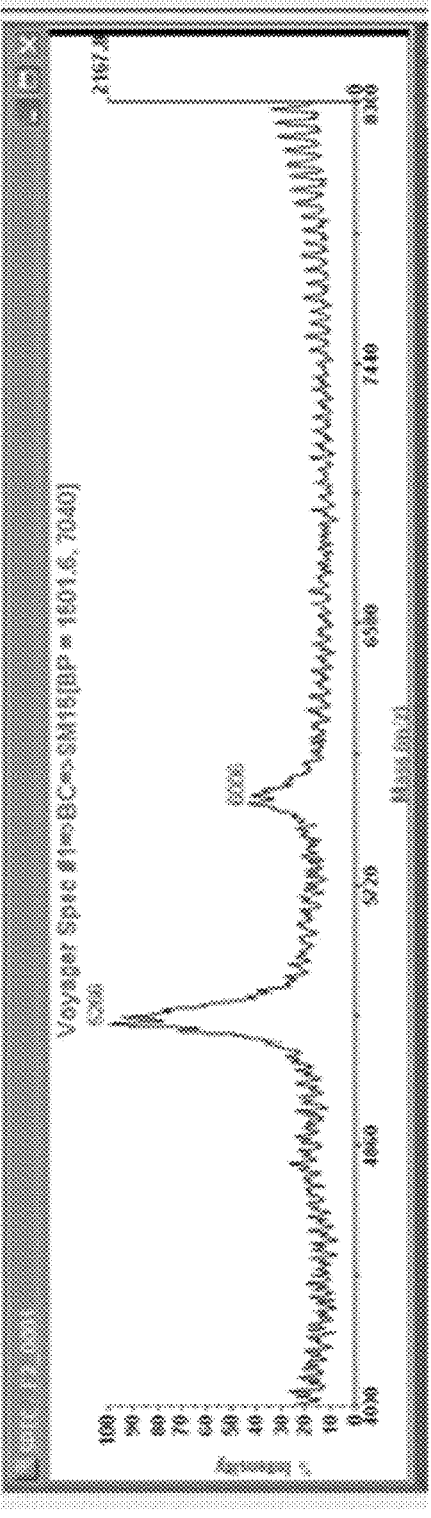
Galβ1-4Glcβ-
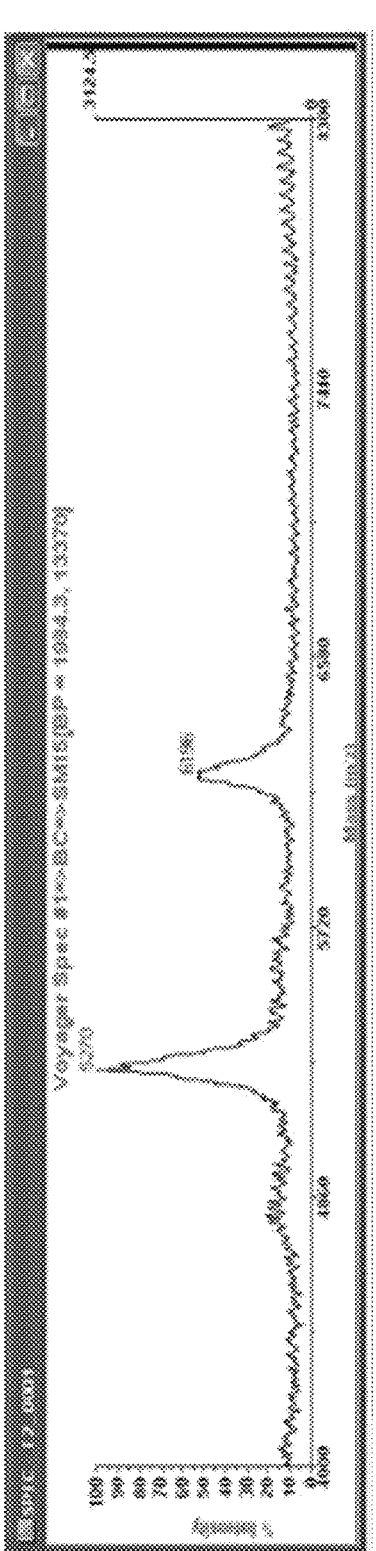
GlcNAcβ1-3Galβ1-4Glcβ-
Figure 7D(a)

D
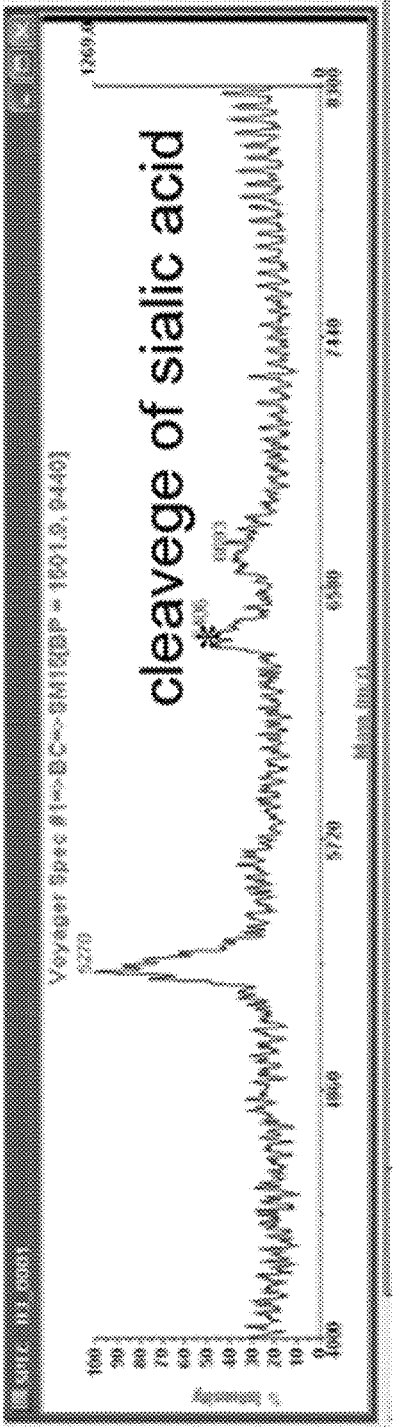
cleavege of sialic acid
NeuAcα2-3Galβ1-3GlcNAcβ1-3Galβ1-4GlcNAcβ~
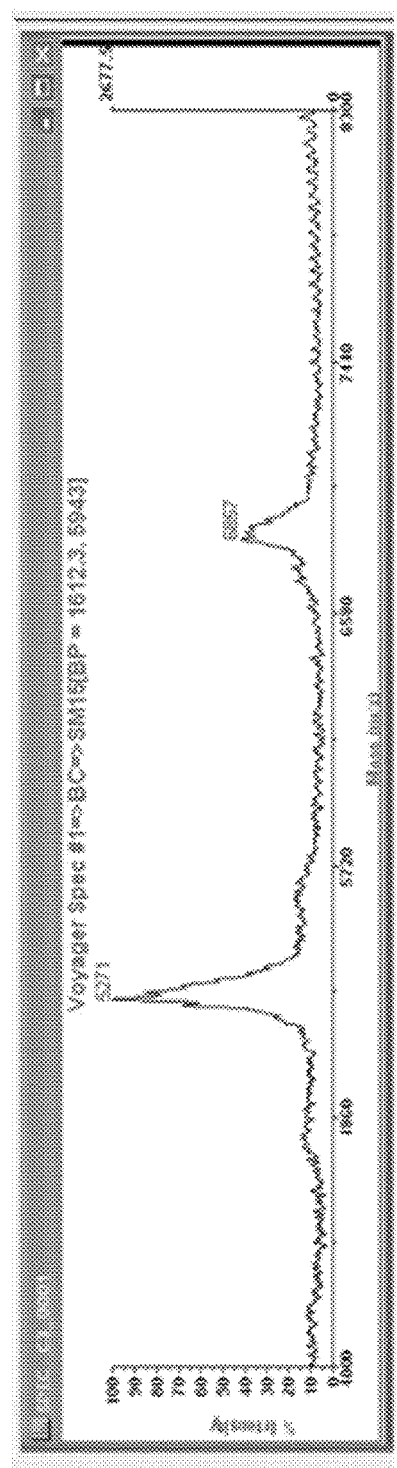
Fucα1-2Galβ1-4[Fucα1-3]GlcNAcβ1-3Galβ1-4[Fucα1-3]GlcNAcβ~
Figure 7D(b)

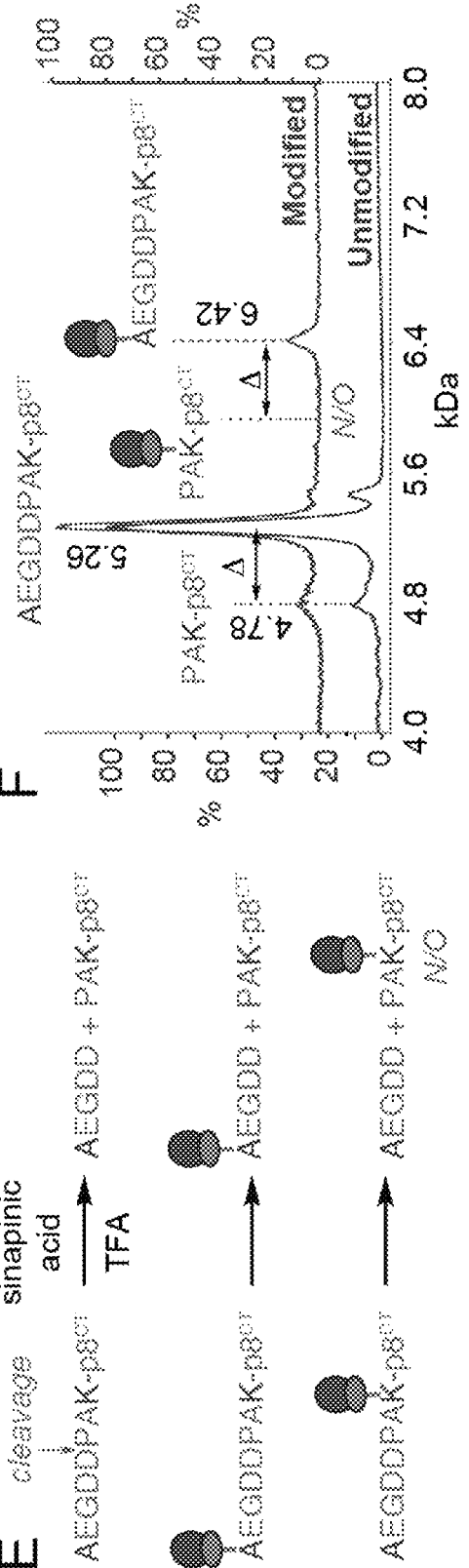
Figure 7E-F

SEQUENCE LISTING

```
<160> NUMBER OF SEQ ID NOS: 48

<210> SEQ ID NO 1
<211> LENGTH: 60
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
```

```
<221> NAME/KEY: misc_feature
<222> LOCATION: (42)..(42)
<223> OTHER INFORMATION: n is a, c, g, or t

<400> SEQUENCE: 1
gagattttca acgtgaaaaa actnctntty gcnathccnc tngtggtacc tttctattct          60

<210> SEQ ID NO 2
<211> LENGTH: 23
<212> TYPE: DNA
<213> ORGANISM: Artificial Sequence
<220> FEATURE:
<223> OTHER INFORMATION: Synthesized

<400> SEQUENCE: 2
ttaagactcc ttattacgca gta                                                 23

<210> SEQ ID NO 3
<211> LENGTH: 23
<212> TYPE: DNA
<213> ORGANISM: Artificial Sequence
<220> FEATURE:
<223> OTHER INFORMATION: Synthesized

<400> SEQUENCE: 3
ttgctaacat actgcgtaat aag                                                 23

<210> SEQ ID NO 4
<211> LENGTH: 21
<212> TYPE: DNA
<213> ORGANISM: Artificial Sequence
<220> FEATURE:
<223> OTHER INFORMATION: Synthesized

<400> SEQUENCE: 4 tttttttcacg ttgaaaatct c                                                  21

<210> SEQ ID NO 5
<211> LENGTH: 30
<212> TYPE: DNA
<213> ORGANISM: Artificial Sequence
<220> FEATURE:
<223> OTHER INFORMATION: Synthesized

<400> SEQUENCE: 5
cagtttacgt agctgcatca gggtggaggt                                          30

<210> SEQ ID NO 6
<211> LENGTH: 9
<212> TYPE: PRT
<213> ORGANISM: Artificial Sequence
<220> FEATURE:
<223> OTHER INFORMATION: Synthesized

<400> SEQUENCE: 6

Gln Phe Thr Leu His Gln Gly Gly Gly
1               5

<210> SEQ ID NO 7
<211> LENGTH: 15
<212> TYPE: PRT
<213> ORGANISM: Artificial Sequence
<220> FEATURE:
<223> OTHER INFORMATION: Synthesized

<400> SEQUENCE: 7
```

```
Ser Val Glu Lys Asn Asp Gln Lys Thr Tyr His Ala Gly Gly Gly
1               5                   10                  15
```

```
<210> SEQ ID NO 8
<211> LENGTH: 89
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t

<400> SEQUENCE: 8
gtggtacctt tctattctca ctcgagygtn garaaraayg aycaraarac ntaycaygcn          60
ggnggnggnt cggccgaaac tgttgaaag                                            89

<210> SEQ ID NO 9
<211> LENGTH: 21
<212> TYPE: DNA
<213> ORGANISM: Artificial Sequence
<220> FEATURE:
<223> OTHER INFORMATION: Synthesized

<400> SEQUENCE: 9
cgagtgagaa tagaaaggta c                                                    21

<210> SEQ ID NO 10
<211> LENGTH: 21
<212> TYPE: DNA
<213> ORGANISM: Artificial Sequence
<220> FEATURE:
<223> OTHER INFORMATION: Synthesized

<400> SEQUENCE: 10
ctgctgttcg caataccact c                                                    21

<210> SEQ ID NO 11
<211> LENGTH: 21
<212> TYPE: DNA
<213> ORGANISM: Artificial Sequence
<220> FEATURE:
<223> OTHER INFORMATION: Synthesized

<400> SEQUENCE: 11
cttctattcg caattccgct c                                                    21

<210> SEQ ID NO 12
```

-continued

```
<211> LENGTH: 21
<212> TYPE: DNA
<213> ORGANISM: Artificial Sequence
<220> FEATURE:
<223> OTHER INFORMATION: Synthesized

<400> SEQUENCE: 12
ctgcttttcg caattccgct t                                                      21

<210> SEQ ID NO 13
<211> LENGTH: 21
<212> TYPE: DNA
<213> ORGANISM: Artificial Sequence
<220> FEATURE:
<223> OTHER INFORMATION: Synthesized

<400> SEQUENCE: 13
cttctgttcg ccattccgct g                                                      21

<210> SEQ ID NO 14
<211> LENGTH: 21
<212> TYPE: DNA
<213> ORGANISM: Artificial Sequence
<220> FEATURE:
<223> OTHER INFORMATION: Synthesized

<400> SEQUENCE: 14
ctgctgtttg cgattccact g                                                      21

<210> SEQ ID NO 15
<211> LENGTH: 21
<212> TYPE: DNA
<213> ORGANISM: Artificial Sequence
<220> FEATURE:
<223> OTHER INFORMATION: Synthesized

<400> SEQUENCE: 15
ctgctttttg caatacccct c                                                      21

<210> SEQ ID NO 16
<211> LENGTH: 21
<212> TYPE: DNA
<213> ORGANISM: Artificial Sequence
<220> FEATURE:
<223> OTHER INFORMATION: Synthesized

<400> SEQUENCE: 16
cttctttttg caattcctct a                                                      21

<210> SEQ ID NO 17
<211> LENGTH: 21
<212> TYPE: DNA
<213> ORGANISM: Artificial Sequence
<220> FEATURE:
<223> OTHER INFORMATION: Synthesized

<400> SEQUENCE: 17
ctactgtttg ctataccgct g                                                      21

<210> SEQ ID NO 18
<211> LENGTH: 21
<212> TYPE: DNA
<213> ORGANISM: Artificial Sequence
<220> FEATURE:
<223> OTHER INFORMATION: Synthesized

<400> SEQUENCE: 18
```

-continued

```
ctactatttg cgattcccct g                                                21

<210> SEQ ID NO 19
<211> LENGTH: 21
<212> TYPE: DNA
<213> ORGANISM: Artificial Sequence
<220> FEATURE:
<223> OTHER INFORMATION: Synthesized

<400> SEQUENCE: 19
cttctgttcg cgatacctct a                                                21

<210> SEQ ID NO 20
<211> LENGTH: 21
<212> TYPE: DNA
<213> ORGANISM: Artificial Sequence
<220> FEATURE:
<223> OTHER INFORMATION: Synthesized

<400> SEQUENCE: 20
ctacttttcg caattcctct g                                                21

<210> SEQ ID NO 21
<211> LENGTH: 21
<212> TYPE: DNA
<213> ORGANISM: Artificial Sequence
<220> FEATURE:
<223> OTHER INFORMATION: Synthesized

<400> SEQUENCE: 21
ctgctatttg ccattcccct a                                                21

<210> SEQ ID NO 22
<211> LENGTH: 21
<212> TYPE: DNA
<213> ORGANISM: Artificial Sequence
<220> FEATURE:
<223> OTHER INFORMATION: Synthesized

<400> SEQUENCE: 22
ctgctgttcg ccataccect t                                                21

<210> SEQ ID NO 23
<211> LENGTH: 21
<212> TYPE: DNA
<213> ORGANISM: Artificial Sequence
<220> FEATURE:
<223> OTHER INFORMATION: Synthesized

<400> SEQUENCE: 23
ctgctgttcg caatcccgct g                                                21

<210> SEQ ID NO 24
<211> LENGTH: 21
<212> TYPE: DNA
<213> ORGANISM: Artificial Sequence
<220> FEATURE:
<223> OTHER INFORMATION: Synthesized

<400> SEQUENCE: 24
ctactcttcg cgattccgct t                                                21

<210> SEQ ID NO 25
<211> LENGTH: 21
<212> TYPE: DNA
```

-continued

<213> ORGANISM: Artificial Sequence
<220> FEATURE:
<223> OTHER INFORMATION: Synthesized

<400> SEQUENCE: 25
ctgctgtttg ctatccctct g                                                                21

<210> SEQ ID NO 26
<211> LENGTH: 21
<212> TYPE: DNA
<213> ORGANISM: Artificial Sequence
<220> FEATURE:
<223> OTHER INFORMATION: Synthesized

<400> SEQUENCE: 26
ctgctctttg ccatcccgct t                                                                21

<210> SEQ ID NO 27
<211> LENGTH: 21
<212> TYPE: DNA
<213> ORGANISM: Artificial Sequence
<220> FEATURE:
<223> OTHER INFORMATION: Synthesized

<400> SEQUENCE: 27
ctactctttg caattcccct t                                                                21

<210> SEQ ID NO 28
<211> LENGTH: 21
<212> TYPE: DNA
<213> ORGANISM: Artificial Sequence
<220> FEATURE:
<223> OTHER INFORMATION: Synthesized

<400> SEQUENCE: 28
ctactgtttg ctatcccact t                                                                21

<210> SEQ ID NO 29
<211> LENGTH: 21
<212> TYPE: DNA
<213> ORGANISM: Artificial Sequence
<220> FEATURE:
<223> OTHER INFORMATION: Synthesized

<400> SEQUENCE: 29
ctgctctttg caatacctct t                                                                21

<210> SEQ ID NO 30
<211> LENGTH: 21
<212> TYPE: DNA
<213> ORGANISM: Artificial Sequence
<220> FEATURE:
<223> OTHER INFORMATION: Synthesized

<400> SEQUENCE: 30
ctactattcg cgatcccgct c                                                                21

<210> SEQ ID NO 31
<211> LENGTH: 21
<212> TYPE: DNA
<213> ORGANISM: Artificial Sequence
<220> FEATURE:
<223> OTHER INFORMATION: Synthesized

<400> SEQUENCE: 31
ctgcttttcg caatacctct a                                                                21

-continued

```
<210> SEQ ID NO 32
<211> LENGTH: 21
<212> TYPE: DNA
<213> ORGANISM: Artificial Sequence
<220> FEATURE:
<223> OTHER INFORMATION: Synthesized

<400> SEQUENCE: 32
ctgctattcg ctatcccact c                                                    21

<210> SEQ ID NO 33
<211> LENGTH: 21
<212> TYPE: DNA
<213> ORGANISM: Artificial Sequence
<220> FEATURE:
<223> OTHER INFORMATION: Synthesized

<400> SEQUENCE: 33
ctgcttttcg ctattcctct c                                                    21

<210> SEQ ID NO 34
<211> LENGTH: 21
<212> TYPE: DNA
<213> ORGANISM: Artificial Sequence
<220> FEATURE:
<223> OTHER INFORMATION: Synthesized

<400> SEQUENCE: 34
ctactcttcg ccattccact g                                                    21

<210> SEQ ID NO 35
<211> LENGTH: 21
<212> TYPE: DNA
<213> ORGANISM: Artificial Sequence
<220> FEATURE:
<223> OTHER INFORMATION: Synthesized

<400> SEQUENCE: 35
ctgctatttg cgatcccgct g                                                    21

<210> SEQ ID NO 36
<211> LENGTH: 48
<212> TYPE: DNA
<213> ORGANISM: Artificial Sequence
<220> FEATURE:
<223> OTHER INFORMATION: Synthesized

<400> SEQUENCE: 36
gcggataaca atttcacaca ggaaacagct atggtgagca agggcgag                       48

<210> SEQ ID NO 37
<211> LENGTH: 48
<212> TYPE: DNA
<213> ORGANISM: Artificial Sequence
<220> FEATURE:
<223> OTHER INFORMATION: Synthesized

<400> SEQUENCE: 37
ttaaattttt gttaaatcag ctcatttttt acttgtacag ctcgtcca                       48

<210> SEQ ID NO 38
<211> LENGTH: 28
<212> TYPE: DNA
<213> ORGANISM: Artificial Sequence
<220> FEATURE:
```

-continued

```
<223> OTHER INFORMATION: Synthesized

<400> SEQUENCE: 38
aaaatgagct gatttaacaa aaatttaa                                    28

<210> SEQ ID NO 39
<211> LENGTH: 20
<212> TYPE: DNA
<213> ORGANISM: Artificial Sequence
<220> FEATURE:
<223> OTHER INFORMATION: Synthesized

<400> SEQUENCE: 39
agctgtttcc tgtgtgaaat                                            20

<210> SEQ ID NO 40
<211> LENGTH: 21
<212> TYPE: DNA
<213> ORGANISM: Artificial Sequence
<220> FEATURE:
<223> OTHER INFORMATION: Synthesized

<400> SEQUENCE: 40
cttctatttg ctattcctct a                                          21

<210> SEQ ID NO 41
<211> LENGTH: 21
<212> TYPE: DNA
<213> ORGANISM: Artificial Sequence
<220> FEATURE:
<223> OTHER INFORMATION: Synthesized

<400> SEQUENCE: 41
ctactgttcg caatcccgct a                                          21

<210> SEQ ID NO 42
<211> LENGTH: 30
<212> TYPE: DNA
<213> ORGANISM: Artificial Sequence
<220> FEATURE:
<223> OTHER INFORMATION: Synthesized

<400> SEQUENCE: 42
cagtttacgt agctgcatca gggtggaggt                                 30

<210> SEQ ID NO 43
<211> LENGTH: 74
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 43
```

```
tagtggtacc tttctattct cactcgagyt ggtaygayct ntaycayggn ggnggntcgg      60
ccgaaactgt tgaa                                                        74

<210> SEQ ID NO 44
<211> LENGTH: 28
<212> TYPE: DNA
<213> ORGANISM: Artificial Sequence
<220> FEATURE:
<223> OTHER INFORMATION: Synthesized

<400> SEQUENCE: 44
cagaaaattc atttactaac gtctggaa                                         28

<210> SEQ ID NO 45
<211> LENGTH: 24
<212> TYPE: DNA
<213> ORGANISM: Artificial Sequence
<220> FEATURE:
<223> OTHER INFORMATION: Synthesized

<400> SEQUENCE: 45
aaaggaacaa ctaaaggaat tgcg                                             24

<210> SEQ ID NO 46
<211> LENGTH: 75
<212> TYPE: DNA
<213> ORGANISM: Artificial Sequence
<220> FEATURE:
<223> OTHER INFORMATION: Synthesized

<400> SEQUENCE: 46
tattcgcaat tcctttagtt gttcctttgt acagccatag tgcggagacc gtggaaagtt      60
gtttagcaaa acccc                                                       75

<210> SEQ ID NO 47
<211> LENGTH: 17
<212> TYPE: DNA
<213> ORGANISM: Artificial Sequence
<220> FEATURE:
<223> OTHER INFORMATION: Synthesized

<400> SEQUENCE: 47
taaatgaatt ttctgta                                                     17

<210> SEQ ID NO 48
<211> LENGTH: 10
<212> TYPE: PRT
<213> ORGANISM: Artificial Sequence
<220> FEATURE:
<223> OTHER INFORMATION: Synthesized

<400> SEQUENCE: 48

Ser Trp Tyr Asp Leu Tyr His Gly Gly Gly
1               5                   10
```

DISPLAY OF MOLECULES ON SILENTLY GENETICALLY ENCODED NANOSCALE CARRIERS FOR DETERMINING SYNERGISTIC MOLECULAR INTERACTIONS

FIELD

The present application pertains to the field of receptor-ligand interactions and molecular recognition. More particularly, the present application relates to methods for the discovery of ligands or combination of ligands that bind in synergy to a biomolecule of interest.

SEQUENCE LISTING

A Sequence Listing is provided herewith as an ASCII.txt file "88466.14 Sequence Listing Project_ST25.txt" created on Sep. 4, 2025 and having a size of 10.3 KB. The contents of the Sequence Listing.txt file are incorporated by reference herein in their entirety.

BACKGROUND

It is known that many proteins and other macromolecular receptors can interact with more than one ligand. Simultaneous interaction of the receptor with two ligands often produces different biophysical, biochemical and physiological outcomes than the interaction of the same receptor with either of the individual ligands. Such interactions, when the binding of two molecules proves to be more advantageous than the binding of either ligand individually, are termed "synergistic" or "positively cooperative" [1]. These "synergistic" interactions may be of great interest in fields that deal with receptor-ligand interactions (drug discovery, diagnostics, and basic research).

One specific example of a synergistic interaction is that of carbohydrates and proteins. Examples are known where two distinct types of glycans bind to one protein with significantly higher affinity than either one of the glycans alone[2-4]. Among possible factors, the biophysical origin of such an enhancement may be due to allosteric conformational change within the protein structure or interactions of two molecules.

Many known methods in ligand discovery are optimized for discovery of individual ligands that bind to individual proteins[2], referred to here as "spatially-separated libraries". Examples include the screening of libraries of individual molecules on microtiter plates, the screening of molecular arrays, in which each molecule is attached to the surface in a specific location, or the screening of a one-bead-one-compound library where individual macroscopic (micron-sized) beads bear a unique molecule. Upgrading "spatially-separated libraries" technology to permit for screening of synergistic interactions is theoretically possible but, in practice, it can be exponentially more complex. A library of N different molecules contains about $N^2/2$ unique binary combinations. Therefore, for even a small library of 1000 molecules, one needs to produce and test 500,000 binary combinations. This number scales to 200,000,000 for a trinary combination. Thus, to achieve a feasible result, it may be necessary to compromise the complexity of the library (i.e., make the number of tested library members smaller).

A well-known technology complementary to "spatially-separated libraries" is a "mixed library" technology, in which multiple molecules are present in the same solution.

This technology allows screening of a mixture of molecules and is a "display" technology. In a display technology, each molecule is attached covalently or non-covalently to a nanoscale information-bearing tag, such as DNA, RNA, ribosome, or particle of bacteriophage or virus. A variant of such technology is a SELEX (systematic evolution of ligands by exponential enrichment) or analogous procedure for development of RNA or DNA aptamers, where the encoding entity is the DNA or RNA molecule. However, DNA or RNA can have potential interaction with the receptor, which interaction may be wanted or unwanted. These problems are minimized in phage display technology where the different molecules are immobilized on virus or bacteriophage particles of identical composition and DNA or RNA of different composition is contained within the viral capsid of the phage particle.

A mixed library technology is suited for identification of synergistic binding because all molecules are present in the same solution. Identification of synergistic interactions using mixed encoded libraries, however, has not been documented. Several requirements are not obvious: (1) To analyze the synergistic binding, it should be possible to produce a library of N defined components and a nearly identical library with N-m components in which m specific members of the original library are excluded (m<N). (2) A production and application of the mixed library technology has to permit two or more molecules to interact with the same target. For example, Lerner and Brenner, Lam and coworkers, and others teach production of mixed molecular libraries displayed, along with encoding tags, on macroscopic carriers, such as beads of >1 micron in size made of agarose, polystyrene. The size of the carrier bead effectively precludes simultaneous binding of distinct molecules attached to two distinct beads to one protein target of size of <0.01 micron.

One technology for the generation of display libraries on nanoscale carriers of identical composition utilizes a recombinant protein technology that introduces additional DNA into the gene of one of the coat proteins of phage and leads to production of the protein fusion product packaged into the virion or phage particle. Multiple variants of such phage and phagemid display technology are known in the art and they are designed to identify a molecule that binds to the receptor of interest.

Display on phage M13 is a specific example of a genetically-encoded library or "display technology"[5]. Phage display is a well-known technique used in the analysis, display and production of protein antigens, especially human proteins of interest[6]. Through genetic engineering of the M13 phage genome, peptides or proteins of interest are attached individually to a phage virion surface protein molecule (usually Gene III protein, g3p). In such a phage population (phage library), each phage carries a gene for a different peptide or protein –g3p fusion that is exposes on its surface. Modification of the genome typically produces phage particles which are not chemically identical. These differences in chemical composition can contribute to differences in which these particles interact with the target. To alleviate this issue, a silent encoding can be used.

"Silent barcoding" technology[7] has been described. This relates to a method of producing a bacteriophage display system on particles that contain DNA of different compositions inside bacteriophage particle and display peptides of identical composition. This technology allows for convenient chemical modification of existing peptide libraries by different chemical modifiers.

Various methods for tagging molecules by DNA or RNA are known. The tag in these technologies has a distinct chemical composition and can form interactions with targets as well. The technology of SELEX RNA and DNA aptamers teaches that different DNA or RNA sequences can have different degrees of interaction with biomolecules.[8,9] The results of the screens that use molecules tagged by DNA or RNA could be less predictable due to possible unwanted interactions between the target and the "tag".

Determining the glycan binding profile of lectins can be both difficult and time consuming. One current method for such identification employs arrays of glycans chemically bound to a solid surface, often glass. Such glycan arrays are used to determine the preference of specific lectin for a specific glycan or glycans immobilized on the surface using a two-step procedure. Firstly, a multitude of glycans are bound to a surface such that one glycan is present in one spatially distinct location. The glycan array is then "panned" with a labelled biomolecule and the biomolecules preference for a glycan is determined by the detection of the label. The primary advantage of this system is that the glycan binding preference of a lectin or biomolecule to a large number, 50-200 glycans, can be assessed in one single format. The disadvantage of this method, however, is that because the glycans are bound in distinct spatially distinct locations, no information of synergistic or co-operative hetero-glycan binding of different glycans can be determined. Furthermore, because of spatial consideration, glycans are not bound on these arrays at densities high enough for homo-glycan cooperative binding either meaning that the derived binding constants for a glycan can be distorted.

Boving and Hogersson teach display of glycans on fluorescent microbead carriers and its analysis by multiplex flow cytometric suspension assay. Wang and others scale up this method to several hundred glycans. The macrobead display is conceptually identical to bead-based libraries mentioned above (006). Such library has limitations due to steric interference of bead with target precluding identification of synergistic binding and possibly even non-synergistic interactions.

Flitch et al. teach display of glycan molecules on DNA molecules but it is not obvious how to use this monovalent library to encode multivalent presentation of carbohydrates of controlled density, which is often needed for protein-carbohydrate interactions.

There exists a need to provide an effective method of identifying molecules for drug discovery, diagnostic development and basic research that studies protein-ligand interactions.

This background information is provided for the purpose of making known information believed by the applicant to be of possible relevance to the present invention. No admission is necessarily intended, nor should be construed, that any of the preceding information constitutes prior art against the present invention.

SUMMARY

In general terms, the invention may comprise a method for identifying ligands or combination of ligands that bind to a target molecule, and in particular to a method which may determine if ligands bind in synergy to a biomolecule of interest.

In one aspect, the invention may comprise a method for the production of genetically-encoded libraries of molecules displayed on nanoscale objects of identical composition ("silent carriers") and the use of these libraries to elucidate protein-ligand interactions.

In one aspect, the invention may comprise a method of identifying one or more molecular interactions between at least two ligands and a target molecule, the method comprising:

a) providing a plurality of silent carriers, each comprising one of a plurality of unique nucleic acid codes therein, wherein each silent carrier is externally chemically identical;

b) attaching a first ligand to one set of silent carriers comprising a first nucleic acid code to form a first set of carriers;

c) repeating step (b) to produce N sets, where N≥2, wherein each set comprises a different ligand, or a different density of ligand, and each set comprises a different nucleic acid code;

d) pooling the N sets to form a first mixed library; and e) contacting the first mixed library with the target molecule and identifying the ligands which bind to the target molecule.

In some embodiments, the method further comprises the steps of pooling the sets of the binding ligands, omitting one set of one binding ligand, to form a second mixed library, and contacting the second mixed library with the target molecule; and determining which binding ligands have lesser or greater affinity for the target molecule in the absence of the omitted ligand.

The encoding moiety or silent carrier has nanoscale size, which is likely to provide less steric interference and likely to be more suitable for general discovery of synergistic binding. If carriers have identical composition, they are less likely to have unwanted molecular interactions with the target that may complicate the analysis.

In some embodiments, the silent carrier is a virus or phage. The plurality of nucleic acid codes may comprise degenerate DNA sequences of a portion of a viral or phage protein and/or unique fluorescent or enzymatic detection markers.

In some embodiments, the ligand is a peptide, carbohydrate or any other biomolecule. The target molecule may be a protein or other biomolecule, cell, organ, or any organic or inorganic material. In one preferred embodiment, the ligands comprise glycans and the target molecules comprise a lectin.

In some embodiments, the identification of binding ligands is performed by extracting nucleic acids from carrier comprising the ligand bound to the target, and amplifying and sequencing the nucleic acids. A quantitative assessment of the binding of the ligands may be assessed by copy number following PCR. Alternatively, or in addition, the identification of binding ligands is performed by detecting the fluorescent or enzymatic detection marker, such a reporter protein encoded into the DNA of the carrier such that the detection marker is expressed by a host organism upon infection by carrier. The reporter protein may comprises galactosidase, chloramphenicol acetyltransferase, or a fluorescent protein, or any other reporter protein or selection marker known to those skilled in the art.

In some embodiments, the identification of binding ligands comprises a step of separating target molecule-ligand-silent carrier complexes in a pull-down assay, which may comprise a step of binding to a solid support, precipitation, centrifugation, magnetic capture, partitioning into another solvent, or any other separation method known to those skilled in the art.

In some embodiments, the first mixed library is a liquid mixed library and the target molecule is comprised in a liquid, which target molecule is converted to solid form and separated from the liquid mixture together with ligands which bind to the target molecule. The target molecule may be in solution, dispersion, emulsion in the liquid, or is a liquid itself. In one embodiment, the target molecule is a salt which is precipitated from solution, such as calcium carbonate. In one embodiment, the target molecules are aggregated into an insoluble particle. In one embodiment, the target molecules are converted from liquid phase to solid phase, such as water which changes to ice.

In another aspect, the invention may comprise a method of displaying a ligand on a virus silently encoded with a nucleic acid code, wherein the nucleic acid code is a degenerate sequence encoding a portion of a native coat protein, or is present in a region of the viral genome which does not encode any protein, or is present in a region of the viral genome the encodes a peptide that is not borne on the virus. This permits use of this display technology with viruses that are not compatible with a display technology that requires expression of a foreign protein borne on the virus.

The carriers may be chemically modified to display a specific ligand on the surface of the carrier at a specific density of ligands per carrier particle. The unique nucleic acid code within the carrier thus can identify either or both of a) the identity of the ligand and/or b) the density of the ligands displayed on the carrier. After the first mixed library is mixed with the target molecule, bound ligands may be separated from unbound ligands, followed by purification of nucleic acids from the bound ligand carriers. The nucleic acid may then be amplified, such as by using PCR and the assessment of the binding of the ligands may be done by copy number of the unique nucleic acid codes.

In another aspect, the invention may comprise a method of calibrating a library of molecular targets comprising adding a carrier (such as a phage) modified with a known ligand to the library (a control phage), followed by screening the library with the ligand of the control phage. The known ligand may be a peptide, carbohydrate or any biomolecule.

In accordance with certain aspects, the present application provides "silent carriers" which are preferably viral or bacteriophage virions of identical external chemical composition containing nucleic acid codes comprising degenerate DNA tags within the genome, packaged inside these particles. The genome of the virus or phage may be manipulated in a manner that does not produce changes in chemical composition of the virion coat, such as, the use of degenerate codons in virion coat coding regions, change in DNA sequence that encodes excised sequences, change in DNA sequence that does not encode expressed protein sequences or change in DNA sequence that encodes components that are not incorporated into the virion coat. Thus, there may be provided a carrier library comprising a plurality of carriers (such as phages or viruses), wherein all the carriers are externally chemically identical prior to the attachment of any ligands, but contain silently encoding distinct nucleic acid molecules therein.

Thus, the invention may provide a library which facilitates the discovery of "synergistic" interactions where two or more molecules can simultaneously bind to one target. Such synergistic binding is typically known to enhance binding affinity, as compared to the interaction of individual ligands. In accordance with other aspects, the present application provides a method for identifying protein-ligand interactions which can be used to provide a more clear understanding whether the interactions of any given ligand from the library with the protein is synergistic or non-synergistic with respect to other ligands present in the same library.

The screens for synergistic binders described herein are best suited for "manually mixed libraries", such as those produced by silent encoding or RNA/DNA-tagging technology and subsequent mixing. It may be possible to apply such screens to expressed displayed libraries such as phage displayed libraries of peptides or proteins, or mRNA or DNA-displayed libraries of polypeptides. Unlike a "silently encoded" chemical library technology, the production of new libraries that contains only defined components and/or is missing one of the component requires significant effort. One example of a large-scale synthesis of specific combinations of DNA is known as array synthesis, and re-expression of the library. These contain steps that are more laborious than simple mixing of N or smaller number of M components from a pre-tagged set.

BRIEF DESCRIPTION OF THE FIGURES

For a better understanding of the present invention, as well as other aspects and further features thereof, reference is made to the following description which is to be used in conjunction with the accompanying drawings, where:

FIG. 1 provides a scheme related to the construction of nucleic acid codes (silent barcodes) within the g3p leader peptide sequence, showing an example of how 6144 possible barcode sequences could be generated: 4 (CTN)×4 (CTN)×2 (TTY)×4 (GCN)×3 (ATH)×4 (CCN)×4(CTN)= 6144.

FIG. 6 shows (A) a schematic description of the genome of bacteriophage m13 and locations for introduction of silent barcodes. (B) Different reporter proteins can be used to track either different chemical modifications or densities of these same modifications. (C) colorimetric or fluorescent reporters can be combined with silent barcodes that are analyzed by sequencing. (D) A four color scheme monitored the enrichment of the LiGA1 mixture described in C on polystyrene plate coated by mannose-binding lectin ConA. The number of particles in the input and output was estimated by plaque forming assay. (E) % Recovery of particles (F) % Recovery in an analogous experiment repeated with LiGA2, which contains ConA binding ligands in the alpha-Gal(+) population. (G) The same four color scheme can be used to monitor and optimize recovery of library on any target, such as cells that contain Mannose-binding lectin DC-SIGN.

FIG. 7 (A) Scheme of chemical ligation strategy used for incorporation of azido-glycans onto pVIII protein of the phage to create a liquid array of glycans. (B) Chemical schematics of the amino acid sequence of p8 protein, their modification by dibenzocyclooctyne N-hydroxysucciniimide (DBCO-HNS) linker, and ligation of a glycan with anomorically linked azide linker to DBCO-modified p8 protein. (C) Characterization of conjugates via MALDI. MALDI detects unmodified p8, partially modified intermediate DBCO-p8 and fully modified conjugate. The ratio of the peaks in MALDI permits characterization of incomplete reactions and it allows estimating the final densities of the glycans on phage. (D) Examples of characterization of phage modified with mono-, d-, tri and tetrasacharides (E) Exposure of p8 protein to acidic conditions in the presence of cinnapinic acid matrix leads to partial cleavage of the p8 protein in a specific location. (F) MALDI spectrum characterizing the partial cleavage of p8 and showing of a specific fragment, from which the regioselectivity of modification of p8 can be concluded.

DETAILED DESCRIPTION

Figure 2:
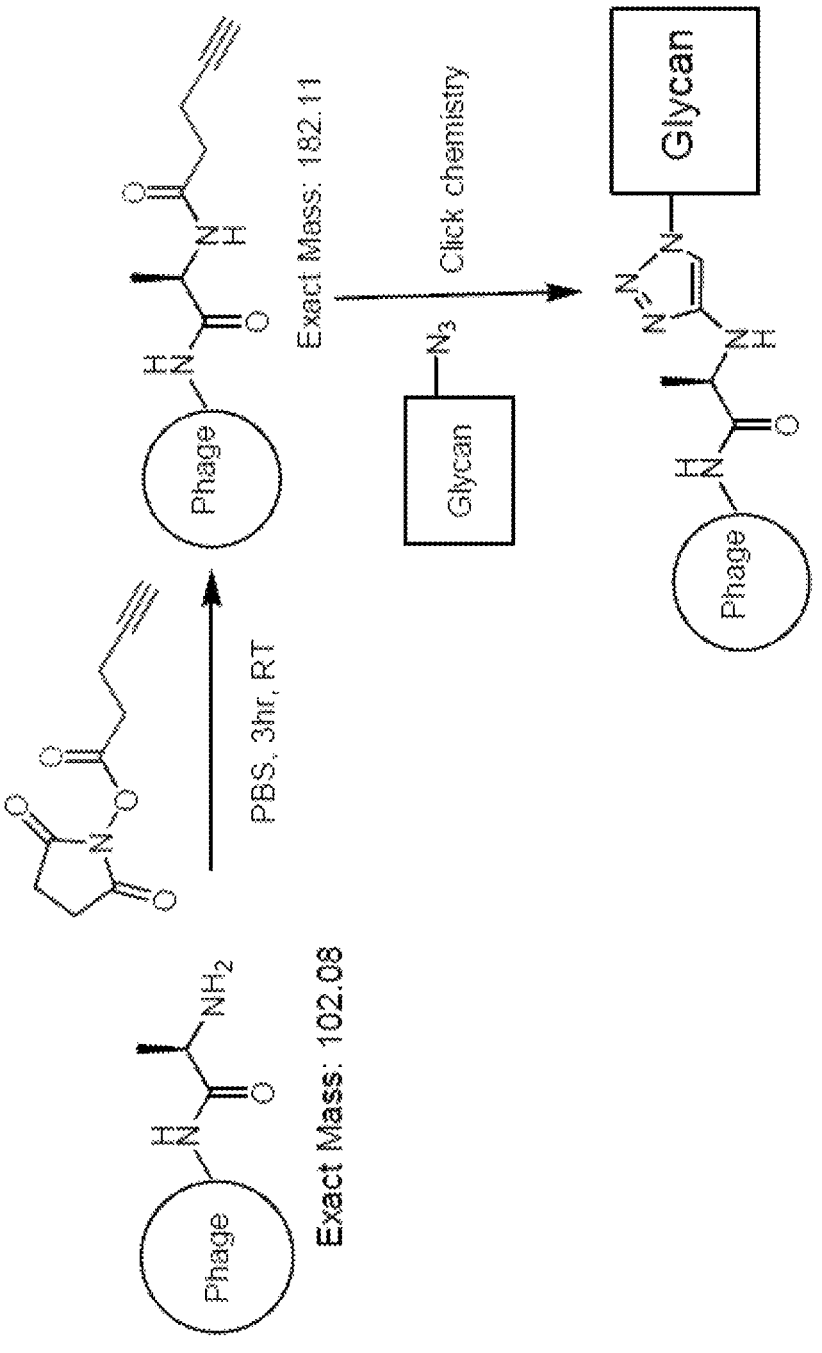
FIG. 2 provides an exemplary scheme of crosslinking carbohydrates to silently barcoded phage.

Unless defined otherwise, all technical and scientific terms used herein have the same meaning as commonly understood by one of ordinary skill in the art to which this invention belongs.

As used herein, a "silent carrier" may include viruses from nearly all available genuses of viruses, including those that cannot be manipulated to produce display or cannot be manipulated effectively by currently available recombinant DNA technology, which viruses include "silent encoding", that is a nucleic acid code which is not expressed or which does not result in a peptide displayed on the surface of the virus. Accordingly, the silent carriers of the present invention do not require the presence of cloned peptide libraries, the introduction of new DNA segments or peptide variable regions. Suitable viruses include phages, but may also include other viruses.

Conventionally, "silent barcodes" are positioned within close proximity to the variable region, which is a foreign DNA fragment, to allow for simultaneous characterization of these two regions by DNA sequencing. However, "silent barcodes" can be introduced at any location within the phage genome, including translationally active and silent regions, auxiliary proteins not used in phage assembly or in sequences excised from phage proteins (e.g. leader peptides).

In the present invention, vruses and bacteriophages also do not have to originate from a genus known to be amenable to efficient DNA manipulation. The host organism producing such viruses has to only uptake the modified DNA to an extent sufficient for production of at least one modified particle. An example is modification of DNA of Archaeal viruses via synthesis and heterologous manipulation within an *E. coli* host to introduce redundant codons into the coding regions. Reintroduction of this DNA back to an Archaeal host, albeit with very low efficiency, can produce a set of silent Archaea viruses with identical composition of the coat and different DNA composition in the genome. Once generated, such silent viruses can propagate via reinfection of its host and require no further recombinant DNA technology for scale-up production.

As described herein, embodiments of suitable silent carriers typically have no preference for the location of nucleic acid codes used for "silent encoding" because the silent carriers do not use any variable regions or include any foreign DNA fragment. As a result, the nature of the phage or virus used for silent carriers is irrelevant. Thus, in certain embodiments, the carriers do not require virus which is compatible with any display technology, such as viruses which are amenable to manipulation via recombinant DNA technology. For example, a class of plant virus is known to be unamenable to display of any foreign sequences because their host, plant cells, proteolytically cleaves nearly all foreign peptide sequences during production of viral particles. Those sequences that are not cleaved can severely interfere with packaging of the particle. These viruses can be still used as silent carriers in accordance with the present application because a silent DNA code can be introduced in a natural protein sequence of regions of DNA that do not produce any sequences. As these changes do not produce any changes in external chemical composition, they are neither excised nor do they typically interfere with the assembly. The virus remains unaltered externally.

In certain embodiments, silent encoding may include the production of silent carriers which utilize DNA codes in the encoding DNA of the coat protein themselves, in regions of DNA that do not encode any protein, or in regions of genome that encode an entity that is not present in the assembled particle, such as spliced RNA sequences or post-translationally excised peptide leader sequences.

This silent encoding permits working not only with M13 phage or other phages that permit display, but with any viruses that can be expressed in laboratory including a large body of known plant, animal and Archaeal viruses, as well as bacteriophages that do not permit display of foreign peptide sequences on their coat protein. Silent variations may be still incorporated in DNA or RNA of these bacteriophages or viruses and produce particles of externally identical chemical composition, with distinct nucleic acid codes inside.

Silently encoded carriers may be chemically modified with a ligand, such as by using standard protein ligation strategies known in the art. A plurality of such carriers, modified with different ligands and encoded with different nucleic acid codes, can be mixed together to create a silently encoded mixed library of molecules of desired composition. Methods presented herein describe the production and utility of such libraries to find synergistic and non-synergistic interaction of these ligands with any target of interest in simple screens.

In some embodiments, a ligand may be attached to a carrier by forming a covalent amide bond with lysine or amino terminus of a carrier coat protein. The carrier coat protein is modified to introduce a reactive handle which is reactive with a cognate reactive handle on the ligand. The cognate reactive handle should not be reactive with any other functional group on the coat protein. For example, the reactive handle is strained alkyne and the cognate reactive moiety is azide.

In certain embodiments, a method as described herein may also work with mixtures of molecules that are tagged by DNA or RNA. In such screens the "information tag" which is a nucleic acid, is not hidden inside the bacteriophage capsid. As a result it is not "silent", and may be less desirable because it may interact with the ligands and target molecules.

In certain embodiments, there is provided a collection of different bacteriophage particles that carry unique nucleic acid codes, which act as "silent barcodes". They are produced separately and modified with different molecules, for example, glycan modifications. Pooling these modified libraries together creates a mixed library. In one preferred embodiment, the mixed library comprises a "liquid glycan array" in which the glycan modifications can be traced by sequencing of the silent barcode.

In certain embodiments, the present method provides a display on "silent carriers" which comprises the mixing of N different sets of silent carriers, each set bearing a different ligand, or a different density of ligand. In certain embodiments, the different sets of ligands are mixed in equal ratios to simplify downstream analysis, but other related ratios may be implemented. With this mixture that contains N different ligands in the same solution, a one-step selection is performed with a target molecule to identify a subset of M potential ligands. Standard selection methods known in the art may be used, such as a pull-down assay and next generation sequencing of isolated, mixed DNA molecules to identify the nucleic acid codes associated with the ligands which bound to the target. The identified M molecules have some affinity for the target molecule and may be "synergistic binders" or "non-synergistic binders". For example, a collection of m molecules is a set which contains molecules M1, M2, M3 . . . Mm (i.e, if m=10, you have, M1, M2, M3, M4, . . . M10). The set of m molecules may be designated as {M}. Thus, there can be sets {M} and subsets {M−Mi} which is the set {M} excluding one set member Mi.

In this particular embodiment, mixing the liquid glycan array having N different glycans, for example, with a protein of unknown carbohydrate binding properties, followed by pull-down of this protein, enriches M binding glycans (M1, M2, M3, etc). To test whether M1 is a glycan that acts synergistically with components M2, M3 and so on, a mixed sub-set of all M glycans and the same set excluding glycan M1 ("M−M1") is made. A pull-down of these mixtures identifies whether glycan M1 acts synergistically or antagonistically with the other glycans. As the process is a simple mixing, this mixing and pull down can be repeated m times to clearly identify all interactions as "synergistic" or "non-synergistic".

A "pull-down" assay includes one where one or the other of a ligand and its target is immobilized or bound to a solid support, such as a bead, to facilitate separation of bound carrier-ligand-target complexes from unbound ligands. For example, hexa-histidine tags can be provided on a target molecule and a hexa-histidine binding molecule, such as nitrilotriacetic acid (NTA) on a bead. Other possibilities may include biotinylation of the protein, and streptavidin-bead; or Fc-fusion of the protein and protein G-bead. Two reactants that are known to form bonds in heterogeneous reaction conditions, known as "bioorthogonal ligations" may be used; one example is tetrazine and trans-cyclooctene pair of bio-orthogonally-reacting components: tetrazine may be placed on the proteins, cyclooctane may be immobilized on the bead. Another example is the use of cyclooctyne and azide: cyclooctane may be used to functionalize the protein, and azide may be placed on the surface of the bead. However, it is understood that these are part of a non-exhaustive list of examples and they are meant to illustrate that other processes that employ specific, strong, complementary covalent or noncovalent interaction may also be suitable to be used for pull-down.

Identification of nucleic acid codes following a pull-down screen may involve deep sequencing or next generation sequencing. For example, if beads are used in the selection step, the beads may then be exposed to biochemical extraction conditions to segregate DNA material from the bead, and the extracted DNA is then subjected to a polymerase chain reaction which amplifies extracted DNA and attaches new sequences to the extracted DNA, termed "adapter" sequences, that permit sequencing of this DNA using next generation sequencing technologies such as Illumina, or Ion Torrent. Post-processing, PCR or incorporation of adapter sequences are optional steps; one example is the conversion of a phage genome to DNA compatible with Illumina sequencing. Another example may include the modification of Illumina sequencing technology to use existing phage DNA as adapter. Alternatively, Illumina adapters may be present in phage DNA. Both examples of the modifications to the procedure may be used to alleviate the need for PCR-steps or others that introduce "adapter sequences". The separation of DNA from the beads is likely to differ when different genuses of bacteriophage are used or different downstream DNA-handling method are used (e.g., PCR with specific reagents). Such separation of DNA from the bead may be readily optimized in accordance with methods known in the art. Following PCR, a suitable "hit" may be identified if a copy number of DNA molecules associated with a particular nucleic acid code exceeds a minimum threshold or ratio.

In certain exemplary embodiments, the present application provides the use of a "liquid" based format for glycan arrays. In a liquid-based format, multiple glycans attached to freely diffusing silent carriers, such as phages, can simultaneously bind to a target biomolecule allowing for both hetero and homo-glycan binding co-operatively to occur. For a liquid format to work, a method to determine which glycans, for example, are bound to a target is typically required. The present application thus provides, in certain embodiments, a construction of an array using silent encoding of glycans; a collection of chemically identical particles subsequently modified with different glycans and then mixed together to form a mixture of N glycans in the same solution. With this mixture that contains N glycans in the same solution, one performs a one-step selection—consisting of pull-down and next generation sequencing of isolated, mixed DNA molecules—to identify an enriched subset of M potential binding glycans. Standard selection methods known in the art may be used. The identified M glycans, in this example, are putatively termed either as "synergistic binders" or "non-synergistic binders".

A single step then determines whether any one of the identified ligands, from the subset of {M}, is a synergistic ligand or a non-synergistic ligand. For example, to determine whether ligand Mi from a set of {M} ligands is a "synergistic binder" or "nonsynergistic" binder, a new mixture that contains {M} and {M−Mi} components (the latter missing a ligand Mi) is constructed. The enrichment process is repeated for each to identify ligands enriched in the presence or in the absence of the component Mi. The copy number of each ligand pulled from the {M} and {M−Mi} sets are then compared. If ligands exhibit the same copy number after pull down from each set, then they are defined as "nonsynergistic". Conversely if copy number of ligand in two mixtures is significantly different, then the ligand is defined as "synergistic" (or possibly antagonistic) with component Mi. Molecules for which the enrichment fraction is statistically insignificant between the two experiments are not acting in synergy with molecule Mi can be used to identify a synergistic binding interaction by demonstrating the loss or severe reduction in binding when molecule Mi is not present.

Thus, a library of N ligands is reduced to a subset of M, and a series of selection steps where each member of {M} is omitted in turn provides the synergistic binding capacity of each member of {M} with each other member of {M}. Unlike screens with separated molecular libraries of molecular arrays that scale as ~N², this screen requires only M+1 screens, where M is a significantly smaller number than N.

In certain embodiments, the present invention comprises a method to determine the glycan preferences of lectins, which are of interest as targets for drug discovery. Other classes of molecules may be similarly examined as the target molecule. Technologies analogous to those of "glycan array" termed protein arrays, peptide arrays, small molecule arrays, nucleic acids and similar arrays are known. They are produced and employed similarly to glycan arrays and may be used in the methods herein with minor or no conceptual modifications.

In exemplary embodiments, glycans are chemically linked to filamentous phage M13, such as via the N terminus of g8p or via an exposed lysine residue located at position 8 of g8p. Similar chemical modifications on plant viruses, animal viruses or Archaeal viruses may also be used. This application provides for the production of N glycan variants, each silently encoded with a nucleic acid code, of those viruses as N separate preparations. The variants are mixed together to form a mixed library, which may be a liquid array of N glycans. The rest of the selection process—a pull-down of modified virions and next generation sequencing of isolated, mixed DNA molecules—to identify an enriched subset of M potential ligands, is described herein.

In certain embodiments, examples of a method of the invention may provide the use of targets with known binding affinity and known synergistic interactions to calibrate the system. For example, a liquid array of N glycans are combined with a known calibration target, and the same array is mixed with an unknown target. Using the same "pull-down" assay for each results in separated beads bearing glycans which bind to the calibration target and the unknown target. Comparison of the copy numbers for hits from each of the control target and unknown target may provides information about the relative binding affinity of the unknown target.

In certain embodiments, example of a method may be used to measure multivalent and homo-glycan binding, by encoding carriers bearing a glycan at different densities. In one example, an M13 phage carrier contains approximately 2700 copies of g8p per particle, meaning that it is possible to label between 1 and 2700 glycans per particle. By varying the ratio of chemical crosslinker to particles in the crosslinking reaction, it is possible to control the average amount of crosslinker per particle. Thus in the subsequent glycan linking reaction, if the amount of glycan which is provided is in excess than the available crosslinkers, the average number of glycan moieties amount of crosslinked to the particles, results in different densities of display. By producing several different libraries displaying the same glycan but at different densities with different nucleic acid codes, the effect of multivalent and homo-glycan co-operative binding may be measured.

To gain a better understanding of the invention described herein, the following examples are set forth. It should be understood that these examples are for illustrative purposes only. Therefore, they should not limit the scope of this invention in any way.

EXAMPLES

Example 1: Cloning and Isolation of Silent SDB and SVEK Library

A silently encoded phage library was cloned using the following procedure. The Silent Distal Barcode (SDB) region (FIG. 1 and FIG. 6A) was introduced into M13KE using PCR amplification followed by using NEBuilder HiFi DNA Assembly (NEB). The insert fragment was PCR amplified using primer 1 5'-GAG ATT TTC AAC GTG AAA AAA CTN CTN TTY GCN ATH CCN CTN GTG GTA CCT TTC TAT TCT CA-3' [SEQ ID NO: 1] and Primer 2 5'-TTA AGA CTC CTT ATT ACG CAG TA-3' [SEQ ID NO: 2] while the vector fragment was PCR amplified using forward primer Primer 3 5'-TTG CTA ACA TAC TGC GTA ATA AG-3' [SEQ ID NO: 3] and Primer 4 5'-TTT TTT CAC GTT GAA AAT CTC-3'[SEQ ID NO: 4]. dsDNA from a phage based on M13KE clone containing the stuffer sequence CAG TTT ACG TAG CTG CAT CAG GGT GGA GGT [SEQ ID NO: 5] equating to the peptide QFT*LHQGGG [SEQ ID NO: 6] was used as a template, with * representing a stop codon. PCR amplified fragments were treated with restriction enzyme Dnp1 and then gel purified. NEBuilder Hifi DNA assembly was then carried out according to the manufactures instruction. The resulting ligated DNA was transformed into *E. coli* K12 ER2738 and grow overnight at 37° C. The overnight culture was then centrifuged to separate bacteriophage from host cells. The host cell were then processed by MiniPrep kit to extract dsDNA for the subsequent cloning round. To clone the silently encoded SVEKNDQKTY-HAGGG [SEQ ID NO: 7] peptide was introduced using the following primers. The insert fragment was PCR amplified using forward primer Primer 5 5' GTG GTA CCT TTC TAT TCT CAC TCG AGY GTN GAR AAR AAY GAY CAR AAR ACN TAY CAY GCN GGN GGN GGN TCG GCC GAA ACT GTT GAA AG-3' [SEQ ID NO: 8] and primer 2. The vector fragment was PCR amplified using primers 4 and Primer 6 5'-CGA GTG AGA ATA GAA AGG TAC-3'[SEQ ID NO: 9]. PCR fragment were proceed as before using NEBuilder Hifi DNA assembly except the resulting ligated DNA was transformed into *E. coli* SS320 cell (Lucigen). The resulting overnight culture was centrifuged to remove host cells and PEG precipitated to concentrate released phage. PEG precipitated phage were resuspended in 1×PBS 50% Glycerol and stored at −20° C. The SDB silent encoding in the SDB region results in $6.0 \times 10^3$ possible sequence combinations, whereas the SVEK region results in $4.2 \times 10^6$ possible sequence combinations. Combined the SDB-SVEK libraries maximal space is $2.6 \times 10^{10}$ possible sequence combinations. Monoclonal silently encoded phage were isolated by plaque isolation. Phage were plated at a density of 100 plaque per plate and individually picked. Phage isolates were picked, grow and sequenced.

To increase the accuracy of next generation sequencing only barcodes that are greater than hamming distance 3 apart, hamming distance is defined as the number of changes that needed to convert a string from one sequence to another, where retained. Unique barcoded phage were amplified and concentrated using PEG precipitation.

FIG. 1 provides a scheme related to the construction of silent barcodes within the g3p leader peptide sequence.

Table 1 provides examples of DNA sequences of phage isolates containing silent distal barcodes (SDB) as described in FIG. 1. SDB is a shortened string contain only the degenerate changes in the DNA codons, while SDB region codon sequence contains the full DNA sequences of the SDB region. If one compares the SDB region codon sequence to the SDB sequenced that every third DNA base of the codon sequence corresponds to the SDB.

TABLE 1

DNA sequences of phage isolates containing silent distal barcodes (SDB) as described in FIG. 1

| Barcode number | SDB | SDB region Codon sequence |
|---|---|---|
| 1 | GGCAAAC | CTG CTG TTC GCA ATA CCA CTC |
| 2 | TACATGC | CTT CTA TTC GCA ATT CCG CTC |
| 3 | GTCATGT | CTG CTT TTC GCA ATT CCG CTT |
| 5 | TGCCTGG | CTT CTG TTC GCC ATT CCG CTG |
| 6 | GGTGTAG | CTG CTG TTT GCG ATT CCA CTG |
| 8 | GTTAACC | CTG CTT TTT GCA ATA CCC CTC |
| 9 | TTTATTA | CTT CTT TTT GCA ATT CCT CTA |
| 10 | AGTTAGG | CTA CTG TTT GCT ATA CCG CTG |
| 11 | AATGTCG | CTA CTA TTT GCG ATT CCC CTG |
| 12 | TGCGATA | CTT CTG TTC GCG ATA CCT CTA |
| 13 | ATCATTG | CTA CTT TTC GCA ATT CCT CTG |
| 14 | GATCTCA | CTG CTA TTT GCC ATT CCC CTA |
| 15 | GGCCACT | CTG CTG TTC GCC ATA CCC CTT |
| 16 | GGCACGG | CTG CTG TTC GCA ATC CCG CTG |
| 17 | ACCGTGT | CTA CTC TTC GCG ATT CCG CTT |
| 18 | GGTTCTG | CTG CTG TTT GCT ATC CCT CTG |
| 20 | GCTCCGT | CTG CTC TTT GCC ATC CCG CTT |
| 21 | ACTATCT | CTA CTC TTT GCA ATT CCC CTT |
| 22 | AGTTCAT | CTA CTG TTT GCT ATC CCA CTT |
| 23 | GCTAATT | CTG CTC TTT GCA ATA CCT CTT |
| 24 | AACGCGC | CTA CTA TTC GCG ATC CCG CTC |
| 25 | GTCAATA | CTG CTT TTC GCA ATA CCT CTA |
| 26 | GACTCAC | CTG CTA TTC GCT ATC CCA CTC |

TABLE 1-continued

DNA sequences of phage isolates containing silent distal barcodes (SDB) as described in FIG. 1

| Barcode number | SDB | SDB region Codon sequence |
|---|---|---|
| 27 | GTCTTTC | CTG CTT TTC GCT ATT CCT CTC |
| 28 | ACCCTAG | CTA CTC TTC GCC ATT CCA CTG |
| 29 | GATGCGG | CTG CTA TTT GCG ATC CCG CTG |

Example 2: Construction of Fluorescent Phage Controls for Colorimetric Evaluation of Panning Protocols The Fluorescent phage are derivatives of the filamentous phage vector M13Ke and have the fluorescent protein mCherry and mNeonGreen cloned in place of the lacZα fragment (FIG. 6A). These phage produce plaques which fluoresce upon illumination with the correct wavelength of light. The phage expressing Fluorescent proteins where constructed using the following procedure. Insert fragments were PCR amplified using Primer 7 5'-GCG GAT AAC AAT TTC ACA CAG GAA ACA GCT ATG GTG AGC AAG GGC GAG-3' [SEQ ID NO: 36] and Primer 8 5'-TTA AAT TTT TGT TAA ATC AGC TCA TTT TTT ACT TGT ACA GCT CGT CCA-3'[SEQ ID NO: 37]. Vector mCherry-pBAD was used as the template for the mCherry insert, whereas Vector mNeonGreen-pBAD was used as a template for the mNeonGreen insert. The vector fragment was PCR amplified using Primer 9 5'-AAA ATG AGC TGA TTT AAC AAA AAT TTA A-3' [SEQ ID NO: 38] and Primer 10 5'-AGC TGT TTC CTG TGT GAA AT-3'[SEQ ID NO: 39]. An M13KE derivatives containing the SDB sequence CTT CTA TTT GCT ATT CCT CTA [SEQ ID NO: 40] were used as a template for the vector PCR for the mCherry construct, whereas a derivative containing the SDB sequence CTA CTG TTC GCA ATC CCG CTA [SEQ ID NO: 41] was used as a template for the mNeonGreen construct. Both templates are M13KE derivative contained the stuffer sequence CAG TTT ACG TAG CTG CAT CAG GGT GGA GGT [SEQ ID NO: 42] equating to the peptide QFT*LHQGGG [SEQ ID NO: 6] in peptide region. Isolated phage plaques were picked, amplified and sequenced to ensure accuracy.

The Fluorescent phage were then further modified to expresses the peptide SWYDLYHGGG [SEQ ID NO: 48]. To do this an insert fragment was produced using primer 9 5'-TA GTG GTA CCT TTC TAT TCT CAC TCG AGY TGG TAY GAY CTN TAY CAY GGN GGN GGN TCG GCC GAA ACT GTT GAA-3' [SEQ ID NO: 43] and primer 2. The vector fragment were produced using Primers 4 and Primer 6 with M13 mNeonGreen and mCherry being used as template. After purification fragments where ligated using NEBuilder HiFi and cloned into E. coli 10G F'. Primer 9 contains degenerate sequence 2× (AGY) 1× (TGG) 2× (TAY) 2× (GAY) 4× (CTN) 2×(TAY) 2× (CAY) 4× (GGN) 4× (GGN) 4× (GGN) resulting in a library of 8192 possible sequences. Because the SDB of the Fluorescent phage is fixed this allowed for the individual identification of specific phage in sequencing. The resulting phage were isolated and sequenced.

To increase the accuracy of next generation sequencing only barcodes that are greater than hamming distance 3 apart, hamming distance is defined as the number of changes that needed to convert a string from one sequence to another, where retained. Unique barcoded phage were amplified and concentrated using PEG precipitation.

Example 3: Cloning of M13 Blocking Phage

The Blocking phage is a M13 derivative contains silent mutations within the Illumina primer regions. This means that the primers we use to amplify the peptide region of the phage do not bind to blocking phage genomic DNA rendering them none PCR amplifiable and therefore invisible to Illumina sequence. The M13 Blocking phage were constructed using the following method. M13 dsDNA was used as a template in both PCR reaction. The vector was amplified with Primer 10 5'-CAG AAA ATT CAT TTA CTA ACG TCT GGA A-3' [SEQ ID NO: 44] and Primer 11 5'-AAA GGA ACA ACT AAA GGA ATT GCG-3' [SEQ ID NO: 45]. The insert was amplified using forward Primer 12 5'-TAT TCG CAA TTC CTT TAG TTG TTC CTT TGT ACA GCC ATA GTG CGG AGA CCG TGG AAA GTT GTT TAG CAA AAC CCC A-3' [SEQ ID NO: 46] and Primer 13 5'-TAA ATG AAT TTT CTG TA-3' [SEQ ID NO: 47]. The insert and vector fragments were treated with Dpn1 and gel purified before submitting purified fragments to the NEBuilder Hifi assembly and transforming into *E. coli* XL1 Blue. Isolated plaques were sequenced to ensure accuracy.

Example 4: Coupling of Glycans to Filamentous Phage

The coupling of glycans to filamentous phage virion was accomplished using a two-step procedure and a propargyl-N-hydroxysuccinimide or dibenzocyclooctyne N-hydroxysucciniimide (DBCO-HNS) linker (FIGS. 2 and 7A and B).

FIG. 7A shows generally the scheme of chemical ligation strategy used for incorporation of azido-glycans onto pVIII protein of the phage to create a liquid array of glycans. Each reaction can produce a phage that contains modified and unmodified p8 proteins. A two-step reaction can produced fully modified product ("prod"), partially modified intermediate ("int.") or unreacted p8 protein ("s.m"). The ratio of these species determines the density of modification on phage. FIG. 7B shows chemical schematics of the amino acid sequence of p8 protein, their modification by dibenzocyclooctyne N-hydroxysucciniimide (DBCO-HNS) linker, and ligation of a glycan with anomorically linked azide linker to DBCO-modified p8 protein.

Firstly, phage carrying a single silent barcode are reacted with the linker via the N-hydroxysuccinimide group. This linker covalently attaches to the phage virion by the major virion coat protein pVIII via either the N terminus of pVIII polypeptide sequence. The phage carrying the crosslinker are then reacted, using click chemistry between the propargyl group with azide derivatives of carbohydrates covalently linking the carbohydrates to the phage virion. To optimize this chemistry the glycan β-azidomannoside was used. Phage were first incubated with 1×, 20× and 50× equivalents of dibenzocyclooctyne-sulfo-N-hydroxy-succinimdyl ester for 30 minutes (the equivalents were calculated with respect to the molarity of the total pVIII protein per phage. For example: $10^{12}$ phage contains $2700*10^{12}$ pVIII proteins per 1 mL, which corresponds to $$\frac{(2700*10^{12}*10^{3})}{6.02*10^{23}} = 4.4*10^{-6} \text{ molar}$$

concentration of pVIII. An azido ethylated mannose was then added to this mixture and incubated for 1 h. The reaction mixture was desalted by Zeba spin column to remove unreacted azido ethylated mannose. Conjugated phage were then analyzed using MALDI-TOF using sinapinic acid as the matrix. FIG. 7C shows characterization of conjugates via MALDI. MALDI detects unmodified p8, partially modified intermediate DBCO-p8 and fully modified conjugate. The ratio of the peaks in MALDI permits characterization of incomplete reactions and it allows estimating the final densities of the glycans on phage. The m/z ratio of the target peaks for unmodified pVIII (mol wt 5239), linker-phage (mol wt 5555) and glycan-phage (mol wt 5760) were deconvoluted from an ion adduct spectra (FIG. 7D). The peak height of the glycan-phage peak was found to be proportional to stoichiometry of the linker and glycan used.

Phage pVIII protein contain two solvent exposed amino groups available for modification (FIG. 7B). The first one is the N-terminal amino group and the second one is lysine (eighth from the N-terminal). While running the MALDI in cinnapinic acid matrix (the matrix also contain TFA), we observed an additional peak ~4850 (m/z) that remained the same even after modification. The findings are shown in FIG. 7E. Earlier works by several groups showed acid susceptibility of the peptide bond between aspartic acid (D) and proline (P); however, phage pVIII protein does contain a D-P bond. Breaking of this bond would create two fragments with a mass corresponding to 505 and 4833. Since the mass of the later peak remained unchanged even after glycan modification, we concluded that all modifications are taking place on the N-terminal amino group.

Figure 3:
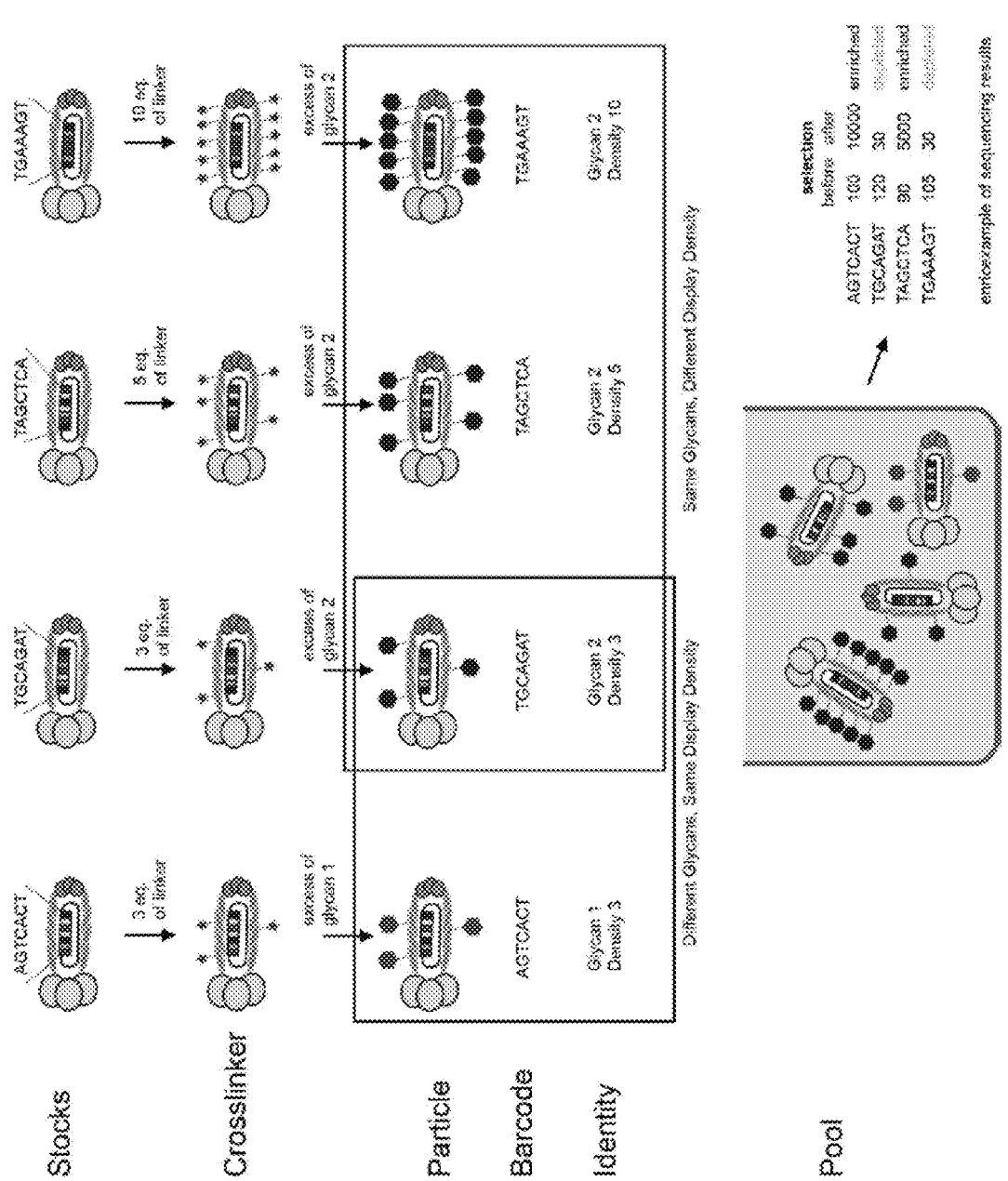
FIG. 3 provides an exemplary scheme of encoding and detecting glycans presented on phage at different densities. Four silent carriers that contain different silent barcodes can be modified with glycan at different densities, or a glycan of different structure. Once the carriers are pooled together, selection and pull-down followed by deep sequencing can be determine which glycan and which density of glycan exhibits the best interactions with the target.

Example 5: Encoding Different Multivalent Density of Ligands Using Silent Carriers The density of display on the phage particles also can be encoded. FIG. 3 provides a description of the effect of controlling the crosslinked chemistry to produce particles displaying the same glycan at different densities.

A mixture of different silent carriers is produced where each silent carrier phage is conjugated with a different glycan or a different densities of glycans as described in FIG. 3. Pooling the mixture together generates the mixture in which each glycan and each different glycan density is associated with a unique carrier, identifiable by its silent barcode. As shown in FIG. 3, P1 is associated with glycan 1, at a density of 3 glycan molecules per phage particle. P2 is associated with glycan 2, at a density of 3 glycan molecules per phage particle. P3 is associated with glycan 2, but at a density of 5 glycan molecules per phage particle, while P4 is associated with glycan 2 at a density of 10 glycan molecules per phage particle.

Example 6: Demonstration of Glycan Modifications Using ELISA

To demonstrate that the modification of the phage did not disrupt the glycan, we conducted ELISA based conformation of glycan binding. We followed a published protocol to complete the ELISA. Firstly a microtiter plate was coated overnight with a dilution gradient of gal4-phage, as well as unmodified phage and linker-phage for negative controls in PBS. The plate was then washed and incubated with 100 µL of the solution containing an anti-Gal4 antibody at 1 µg/ml for 2 hrs. The plate was then washed again and incubated with a secondary antibody HRP-tagged goat anti-mouse (1:5000 dilution) for 40 min. The plate wash then wash and the HRP substrate TMB was added. After development the reaction was stopped with 1(M) phosphoric acid and read at 450 nm and the collected data were processed in origin software.

Figure 4:
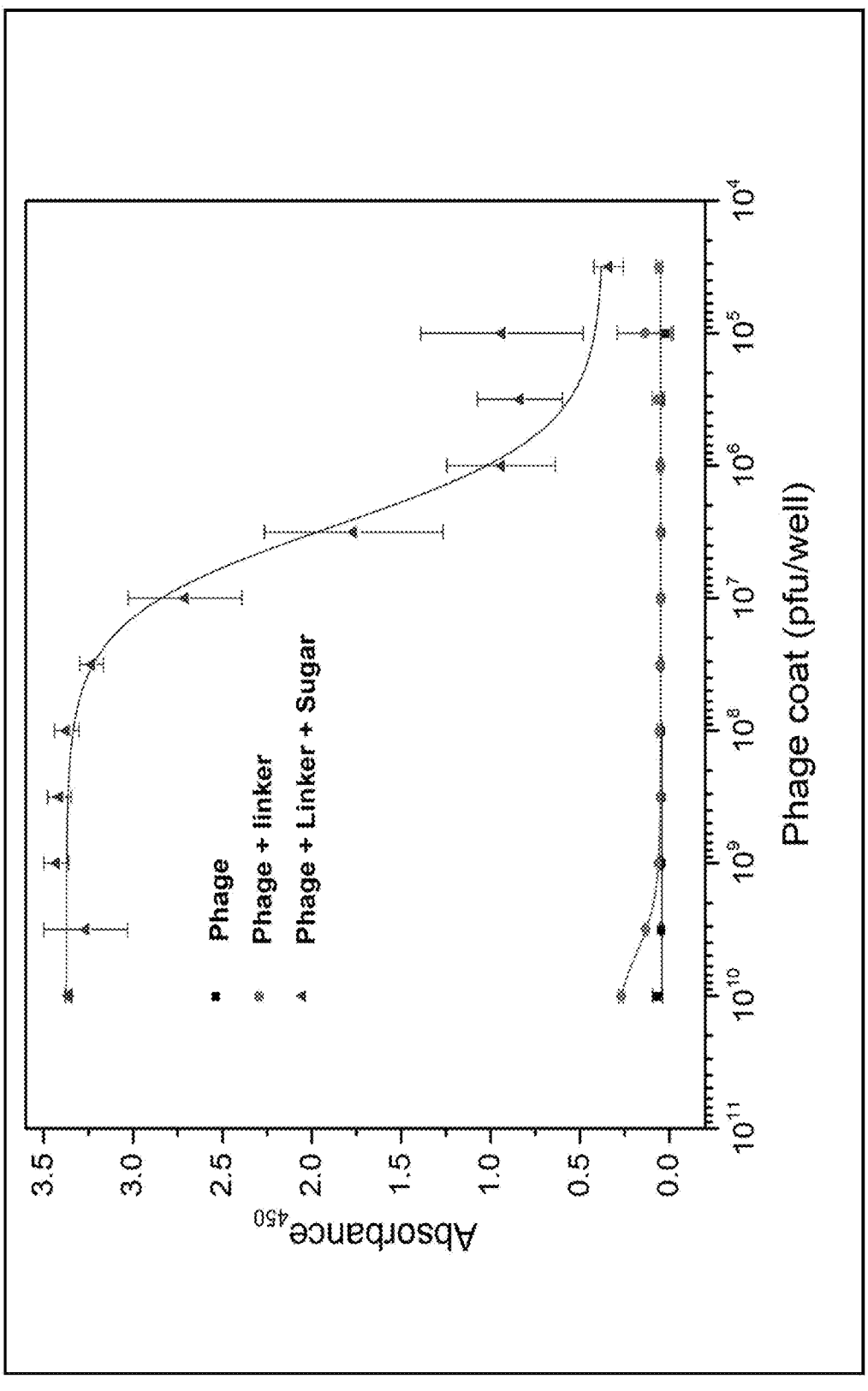
FIG. 4 shows specific recognition of glycan-phage adsorbed on polystyrene plate by glycan specific monoclonal antibody. Unmodified phage and DBCO-phage are used as control. Each data point represents the mean value of triplicates.

FIG. 4 shows specific recognition of glycan-phage adsorbed on polystyrene plate by glycan specific monoclonal antibody. Unmodified phage and DBCO-phage are used as control. Each data point represents the mean value of triplicates.

Figure 5:
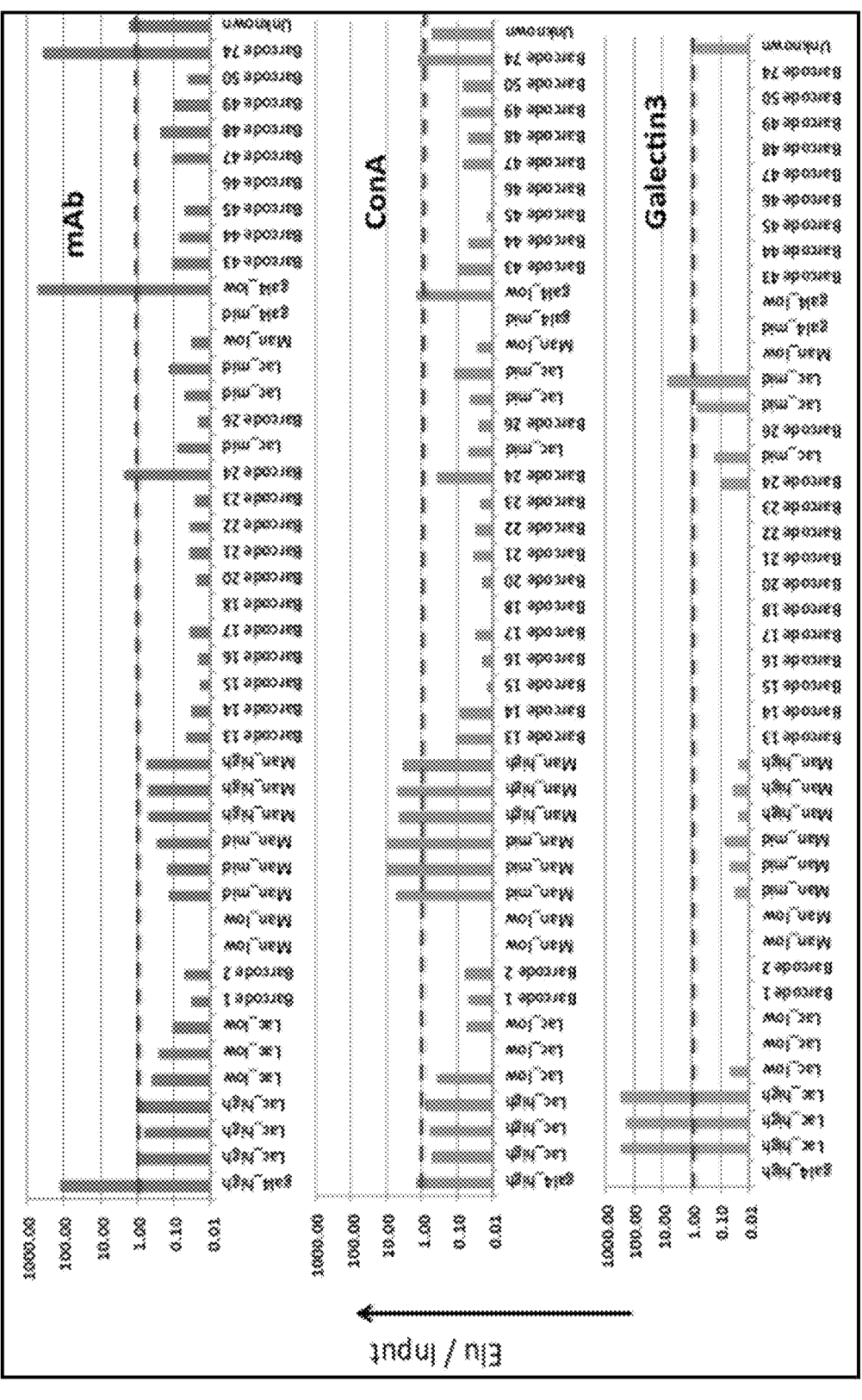
FIG. 5 shows the recovery of glycans from library detected by deep-sequencing. Three glycans used in the mixture are tetra galactofuranose (gal4), beta mannose (man) & lactose (lac).

FIG. 5 shows the recovery of glycans from library detected by deep-sequencing. Three glycans used in the mixture are tetra galactofuranose (gal4), beta mannose (man) & lactose (lac). As targets, we used their corresponding known targets—a murine mAb raised against gal4, ConA & galectin3 respectively. The enrichment for each barcode is calculated by dividing the number of reads found in elution samples by the corresponding number in input sample. The dotted line on each panel shows one fold enrichment.

Example 7: Panning of Glycan Binding Proteins in Solution

Untagged Glycan binding proteins (GBP) were first chemically modified with NHS-PEG4 Biotin, whereas Glycan binding antibodies where not modified. The liquid glycan array (LiGA) was then mixed with 10 µg of the glycan binding protein 1 hr at room temperature. To capture the GBP and the bound LiGA phage, 10 µL of either strep-agarose beads for Biotinylated GBP or ProteinG beads for Glycan binding antibodies, pre-wash in binding buffer were added. Additionally 0.1% BSA was added to the mixture at this point as a blocking agent to reduce nonspecific binding of phage to the beads. After 45 minutes of incubation the mixture was centrifuged at 500 g for 1 min to collect the beads. The supernatant was discarded and the beads were washed with 1 mL of PBST buffer and centrifuged to collect the beads. The washing step was repeated three times. If the experiment was conducted as an optimization experiment to evaluate glycan binding the phage would be eluted from the beads using acid elution. To do this beads were mixed with 0.2M glycine buffer pH 2 for 10 minutes; solution was then neutralized with 1M Tris pH9 and the eluted phage where enumerated by phage plating. Because the LiGA (FIG. 6C) contains the Fluorescent phage conjugated to Mannose (mNeonGreen) and Galactose (mCherry) binding to Mannose and Galactose binding Lectins can be demonstrated using these controls. This allowed for the optimization of panning procedure without the need for deep sequencing (FIG. 6C). Optimization of panning on Concanavalin A (ConA) showed that mNeonGreen phage displaying Mannose was retained at a high amount than mCherry phage displaying Galactose. This result is consistent with ConA being a Mannose binding Lectin.

For samples that were to be deep sequenced, the beads were resuspended into 30 µL of Tris-EDTA buffer (Tris 10 mM+EDTA 0.01 mM pH. 30 µL of Hexane was then added to the beads and incubated shaking at room temperature for 10 minute to allow for disassembly and release of phage genomic DNA. Hexane was then evaporated by incubation at 68 C for 8 min. After evaporation of the solvent beads were pelleted by centrifugation at 21,000 g for 2 min. The remaining supernatant and submitted to PCR amplification to amplify the SDB-SVEK region and attach Illumina deep sequencing adaptors. Deep sequencing on Ulex Europaeus Agglutinin (UEA lectin) showed that phage displaying glycans with terminating or branched Fucose were retained (FIG. 6E), while panning on with an anti-Gal4 antibody showed the retention of Gal4 displaying phage.

FIG. 6A shows a schematic description of the genome of bacteriophage m13 and locations for introduction of silent barcodes. The barcodes can be in the translated regions of the coat proteins, such as p3. They can also be inserted into the regions that do not encode any phage proteins (reporter box at the bottom). Such gene is not present as protein product in phage but it is transduced by phage to host organism. FIG. 6B shows different reporter proteins can be used to track either different chemical modifications or densities of these same modifications. Examples shows how high density (1500 mannose molecules ligated per phage), medium density (500 mannose molecules per phage), low density (200 mannose molecules per phage) and absence or any mannose molecules can be each encoded by four distinct reporter proteins. Phages that contain high mannose modification form green fluorescent plaques because they transduce mNeonGreen gene into the host bacteria. Analogously, medium-Man phage transduces mCherry protein and forms red plaques, low density Man-phage transduces alpha-galactosidase (alpha-Gal) gene and forms blue plaques on agar that contains colorimetric substrate X-gal. Phage that displays no glycan does not transduce any reported and forms white plaques. The ratio of green-red-blue-white plaques before and after selection can be used to monitor the effect of density of mannose on enrichment against specific target.

FIG. 6C shows that colorimetric or fluorescent reporters can be combined with silent barcodes that are analyzed by sequencing. In this examples, two mixtures are created: LiGA1 contains 9 different alpha-Gal (+) carriers modified with either galactose, lactose or LNT tetrasacharide at 3 different densities (1500, 500 or 200 copies per phage). Nine combinations are distinguishable by sequencing of barcode. LiGA1 also contains Mannose1500-mNeonGreen and Lactose1500-mCherry and unmodified "blocking phage" expressing no reporter. Expanded LiGA2 mixtures contains everything that LiGA1 contains plus additional 9 clones that contain beta-Mannose, alphe-mannose and alpha-Man3 glycans at three different densities.

FIG. 6D shows that a four color scheme monitored the enrichment of the LiGA1 mixture shown in FIG. 6C on polystyrene plate coated by mannose-binding lectin ConA. The number of particles in the input and output was estimated by plaque forming assay. FIG. 6E shows that recovery of particles that contain high density of Mannose, detected as green plaques, is 15%. Recovery of red particles that contain lactose glycan that does not bind to ConA is 0.3%. Only 0.04% of the unmodified "blocking" phage particles are recovered; the same low recovery (0.06%) is observed for 9 phage clones in the alpha-Gal(+) "blue" population because this population display no ligands that bind to ConA. FIG. 6F shows the results from an analogous experiment repeated with LiGA2, which contains ConA binding ligands in the alpha-Gal(+) population. Recovery of "blue" population is significantly higher than one observed in FIG. 6E and it is 10-fold higher than recovery of unmodified white phage. Recovery of ConA-binding green clones and non-ConA binding "red" clone are similar to those observed in FIG. 6D.

FIG. 6G shows that the same four color scheme can be used to monitor and optimize recovery of library on any target, such as cells that contain Mannose-binding lectin DC-SIGN. Initial population contains 1:100 ratio of green to white plaques. After 4 washes, the cell pellet p4 contains 1:1 ratio of green (Man) to white (non glycosylated phage) indicating that 100-fold enrichment of Man-phage took place. Fewer Man-green phage clones is recovered on cells that does not contain DC-SIGN. Sequencing of the DNA associated with cell pellet confirms the enrichment, however, colorimetric monitoring can be used to optimize the selection procedure without the need for sequencing.

Figure 6H:
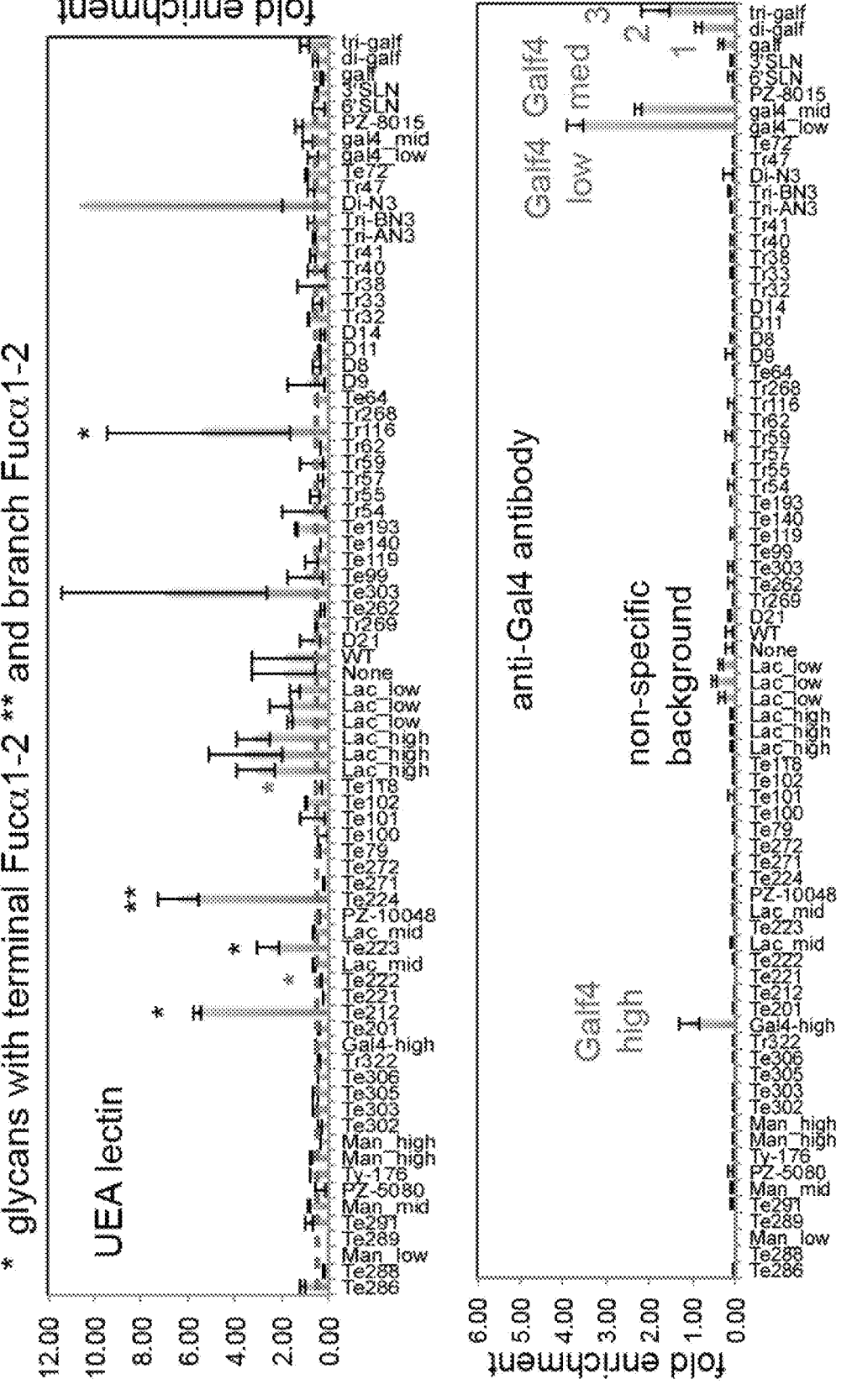
FIG. 6H. Representative example of pull down of an array of 74 glycans by plant lectin UGA that recognizes Fucα1-2-modification and anti-Gal4 antibody.

FIG. 6H shows representative example of pull down of an array of 74 glycans by plant lectin UGA that recognizes Fucα1-2-modification and anti-Gal4 antibody. Specific glycans present in the array to contain Fucα1-2-modification are: Te212: Fucα1-2Galb1-4[Fucα1-3]GlcNAcb1-3 Galb1-4 [Fucα1-3]GlcNAcb-Phag; Te222: GalNAcα1-3 [Fucα1-2]Galβ1-4G1cNAcβ-Phage (enrichment not detected: false negative?); Te223: Gala1-3[Fucα1-2]Galb1-4G1cNAcb-Phage; Te224: GalNAca1-3[Fucα1-2]Galb1-4Glcb-Phage; Te118: Fucα1-2Galb1-4[Fucα1-3]GlcNAcb-Phage (enrichment not detected); Te303: Neu5Aca2-3 [Neu5Aca2-3Galb1-3 GalNAcb 1-4]Galb1-4Glcb-Phage; Tr116: Fucα1-2Galb1-3 GlcNAcb-Phage

Example 8: Demonstration of Cell Based Screening with LiGA

The LiGA can be used to assess the Glycan binding property of live whole cell. To demonstrate this the LiGA array was panned against a Rat 6 Fibroblast stable cell line that highly expresses the Human Dendritic Cell-Specific Intercellular adhesion molecule-3-Grabbing Non-integrin receptor (DC-SIGN). As a negative control a Rat-6 fibroblast line that did not express any protein was used. The details of this cell lines construction is available in [4]. DC SIGN is a C-type lectin which has affinity to High mannose and fucose containing Glycans. To do this experiment Log phase cells were detached from flask using Trypsin and resuspended at $1 \times 10^6$ cell/mL in Hepes Buffer (20 mM HEPES pH 7.4, 150 mM NaCl, 2 mM CaCl, 1% BSA. 1 mL aliquot of cell were then pelleted (1000 rpm/4 min) and resuspend in 500 μL of HEPES Buffer containing $1 \times 10^8$ pfu of LiGA phage and $1 \times 10^8$ pfu of Blocking phage. The LiGA array used in this example contain a positive and negative control Fluorescent phage to monitor the efficiency of the washing (FIG. 6G). The positive control phage was a mNeonGreen Fluorescent phage that has been conjugated to monovalent Mannose. The negative control phage used was a mCherry Fluorescent phage conjugated to Galactose. Cell were then incubated for 2 hours on ice. Cell were then wash 3 times using 4 mL of Hepes Buffer and resuspended in 30 of $H_2O$. A 5 μL sample was removed before each wash step to analyse phage titre. Samples were boiled for 10 minutes followed by centrifugation at 21 000 g for 5 minutes to remove cell debris. The supernatant was then transfer into PCR tubes containing PCR reaction mixture to prepare amplicons for Illumina Sequencing. Titering of the unboiled samples showed that after 3 washes of the cells that the positive phage titre was 10 fold greater than the negative control phage (FIG. 6G). Furthermore the number of blocking phage had reduced from $1 \times 10^8$ pfu to $1 \times 10^5$ pfu. Further washing of the cell did not significant reduce the phage titers. Deep sequencing of the phage remaining bound to the cells showed that phage conjugated to Mannose containing glycans were retained in the panned population whereas phage conjugated to other glycans were not.

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated. To the extent that the following description is of a specific embodiment or a particular use of the invention, it is intended to be illustrative only, and not limiting of the claimed invention.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to combine, affect or connect such aspect, feature, structure, or characteristic with other embodiments, whether or not such connection or combination is explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all ranges described herein, and all language such as "up to", "at least", "greater than", "less than", "more than", "or more", and the like, include the number(s) recited and such terms refer to ranges that can be subsequently broken down into sub-ranges as discussed above.

REFERENCES

All publications, patents and patent applications mentioned in this specification are indicative of the level of skill of those skilled in the art to which this invention pertains and, if permitted, are herein incorporated by reference to the same extent as if each individual publication, patent, or patent applications was specifically and individually indicated to be incorporated by reference.

1. Laskowski, R. A., Gerick, F. & Thornton, J. M. The structural basis of allosteric regulation in proteins. FEBS letters 583, 1692-1698 (2009).
2. Shivatare, S. S. et al. Modular synthesis of N-glycans and arrays for the hetero-ligand binding analysis of HIV antibodies. Nature chemistry 8, 338-346 (2016).
3. Johnson, Q. R., Lindsay, R. J., Petridis, L. & Shen, T. Investigation of Carbohydrate Recognition via Computer Simulation. Molecules 20, 7700-7718 (2015).
4. Watanabe, M., Nakamura, O., Muramoto, K. & Ogawa, T. Allosteric regulation of the carbohydrate-binding ability of a novel conger eel galectin by D-mannoside. The Journal of biological chemistry 287, 31061-31072 (2012).
5. Scott, J. K. & Smith, G. P. Searching for Peptide Ligands with an Epitope Library. Science 15 249, 386-390 (1990).
6. Rakonjac, J., Bennett, N. J., Spagnuolo, J., Gagic, D. & Russel, M. Filamentous Bacteriophage: Biology, Phage Display and Nanotechnology Applications. Curr Issues Mol Biol 13, 51-75 (2011).
7. Tjhung, K. F. et al. Silent Encoding of Chemical Post-Translational Modifications in 20 Phage-Displayed Libraries. Journal of the American Chemical Society 138, 32-35 (2016).
8. Tuerk, C. & Gold, L. Systematic evolution of ligands by exponential enrichment: RNA ligands to bacteriophage T4 DNA polymerase. Science 249, 505-510 (1990).
9. Ellington, A. D. & Szostak, J. W. In vitro selection of RNA molecules that bind specific ligands. Nature 346, 818-822 (1990).
10. Marvin, D. A., Welsh, L. C., Symmons, M. F., Scott, W. R. & Straus, S. K. Molecular structure of fd (f1, M13) filamentous bacteriophage refined with respect to X-ray fibre diffraction and solid-state NMR data supports specific models of phage assembly at the bacterial membrane. Journal of molecular biology 355, 294-309 (2006).
11. Crimmins, D. L., S. M. Mische, and N. D. Denslow, Chemical cleavage of proteins in solution. Curr Protoc Protein Sci, 2005. 11(11).
12. Gardner, M. W. and J. S. Brodbelt, Impact of proline and aspartic acid residues on the dissociation of intermolecularly crosslinked peptides. J Am Soc Mass Spectrom, 2008. 19(3): p. 344-57.
13. Guo, Y., et al., Structural basis for distinct ligand-binding and targeting properties of the receptors DC-SIGN and DC-SIGNR. Nat Struct Mol Biol, 2004. 11(7): p. 591-8.

Lerner and Brenner, Encoded Combinatorial Chemistry. Proc. Natl. Acad. Sci. 1992. 89, pp 5381-5383

Lam et al. The "One-Bead-One-Compound" Combinatorial Library Method. Chem. Rev., 1997, 97 (2), pp 411-448

Boving and Hogersson. PEGylation of microbead surfaces reduces unspecific antibody binding in glycan-based suspension array. J Immunol Methods. 2014 October; 412: 42-52.

Pochechueva et al. Comparison of printed glycan array, suspension array and ELISA in the detection of human anti-glycan antibodies. Glycoconj J. 2011 December; 28(8-9):507

Purohit et al. Multiplex glycan bead array for high throughput and high content analyses of glycan binding proteins. Nature Communications, Volume 9, Article number:258 (2018) Thomas et al. Application of Biocatalysis to on-DNA Carbohydrate Library Synthesis. ChemBioChem 2017, 18, 858.

The embodiments of the invention in which an exclusive property or privilege is claimed are defined as follows:

1. A method of identifying one or more molecular interactions between at least two ligands and a target molecule, the method comprising:

(a) providing a plurality of silent carriers, each comprising one of a plurality of unique nucleic acid codes therein, wherein each silent carrier is externally chemically identical;

(b) attaching a first glycan ligand to one set of silent carriers comprising a first nucleic acid code to form a first set of carriers;

(c) repeating step (b) to produce N sets, where N>2, wherein each set comprises a different glycan ligand, or a different density of glycan ligand, and each set comprises a different nucleic acid code;

(d) pooling the N sets to form a first mixed library comprising a liquid glycan array;

(e) contacting the first mixed library with the target molecule and identifying the set of ligands {M} which bind to the target molecule;

(f) repeatedly creating a pooled set of binding glycans, omitting one binding glycan or one density of binding glycan, to form different mixed libraries, and contacting each mixed library with the target model; and (g) determining, using the different nucleic acid codes, which binding glycans have lesser or greater affinity for the target molecule in the absence of the omitted glycan.

2. The method of claim 1 wherein the carrier is a virus or phage and the target molecule is a lectin.

3. The method of claim 2, wherein the plurality of nucleic acid codes comprises degenerate DNA sequences of a portion of a viral or phage protein.

4. The method of claim 1, wherein at least one nucleic acid code encodes a unique fluorescent or enzymatic detection marker.

5. The method of claim 1 wherein a set of silent carriers comprises carriers chemically modified to display a glycan ligand on the surface of the carrier at a specific density.

6. The method of claim 1, wherein the identification of binding ligands is performed by extracting nucleic acids from carrier comprising the ligand bound to the target, and amplifying and sequencing the nucleic acids.

7. The method of claim 6, wherein a quantitative assessment of the binding of the ligands is assessed by copy number following PCR.

8. The method of claim 4 wherein the identification of binding ligands is performed by detecting the fluorescent or enzymatic detection marker.

9. The method of claim 1, wherein the target molecule is a protein, purified biomolecule, cell, organ, or inorganic material.

10. The method of claim 1 wherein the identification of binding ligands comprises a step of separating target molecule-ligand-silent carrier complexes in a pull-down assay.

11. The method of claim 10 wherein the pull down assay comprises a step of binding to a solid support, precipitation, centrifugation, magnetic capture, or partitioning into another solvent.

12. The method of claim 1 wherein the first mixed library is a liquid mixed library and the target molecule is comprised in a liquid, which target molecule is converted to solid form and separated from the liquid mixture together with ligands which bind to the target molecule.

13. The method of claim 12 wherein the target molecule is in solution, dispersion, emulsion in the liquid, or is a liquid itself.

14. The method of claim 13 wherein the target molecule is a salt which is precipitated from solution.

15. The method of claim 13 wherein the target molecules are aggregated into an insoluble particle.

16. The method of claim 13 wherein the target molecules are converted from liquid phase to solid phase.

17. The method of claim 4 wherein the detection marker comprises a reporter protein encoded into the DNA of the carrier such that the detection marker is expressed by a host organism upon infection by carrier.

18. The method of claim 17 wherein the reporter protein comprises galactosidase, chloramphenicol acetyltransferase, or a fluorescent protein.

19. A method of claim 1 where a ligand is attached to a carrier by forming a covalent amide bond with lysine or amino terminus of a carrier coat protein.

20. The method of claim 19 where the carrier coat protein is modified to introduce a reactive handle which is reactive with a cognate reactive handle on the ligand, which cognate reactive handle is not reactive with any other functional group on the coat protein.

* * * * *